(12) United States Patent
Ragogna et al.

(10) Patent No.: US 8,957,243 B2
(45) Date of Patent: Feb. 17, 2015

(54) PHOSPHONIUM IONIC LIQUIDS AND COATINGS MADE THEREFROM

(75) Inventors: Paul J. Ragogna, Stratford (CA); Jocelyn J. Tindale, Guelph (CA)

(73) Assignee: The University of Western Ontario, London, ON (CA)

( * ) Notice: Subject to any disclaimer, the term of this patent is extended or adjusted under 35 U.S.C. 154(b) by 997 days.

(21) Appl. No.: 12/864,964

(22) PCT Filed: Jan. 28, 2009

(86) PCT No.: PCT/CA2009/000101
§ 371 (c)(1),
(2), (4) Date: Oct. 19, 2010

(87) PCT Pub. No.: WO2009/094768
PCT Pub. Date: Aug. 6, 2009

(65) Prior Publication Data
US 2011/0041912 A1 Feb. 24, 2011

Related U.S. Application Data

(60) Provisional application No. 61/006,703, filed on Jan. 28, 2008.

(51) Int. Cl.
| | | |
|---|---|---|
| *C07C 69/533* | (2006.01) | |
| *C07F 9/54* | (2006.01) | |
| *C09D 5/00* | (2006.01) | |
| *C09K 3/16* | (2006.01) | |
| *C09K 3/18* | (2006.01) | |
| *H01B 1/12* | (2006.01) | |
| *C23C 22/03* | (2006.01) | |
| *C08K 5/50* | (2006.01) | |

(52) U.S. Cl.
CPC ............ *H01B 1/122* (2013.01); *C07F 9/5407* (2013.01); *C09D 5/00* (2013.01); *C23C 22/03* (2013.01); *C08K 5/50* (2013.01)
USPC ............ 560/222; 568/9; 568/11; 106/287.24; 106/287.27; 106/287.28; 106/287.29

(58) Field of Classification Search
None
See application file for complete search history.

(56) References Cited

U.S. PATENT DOCUMENTS

2006/0094866 A1    5/2006    Gladysz et al.

FOREIGN PATENT DOCUMENTS

DE    10212424    12/2003

OTHER PUBLICATIONS

Database CAPLUS on STN, Acc. No. 2006:898499, Emnet el al., Advanced Synthesis & Catalysis (2006), 348 (12+13), p. 1625-1634 (abstract).*
Database CAPLUS in STN, Acc. No. 2003:110367, He et al., Green Chemistry (2003), 5(1), p. 92-94 (abstract).*
Tindale et al., "Synthesis and characterization of fluorinated phosphonium ionic liquids", Can. J. Chem., 2007, pp. 660-667, vol. 85.
Consorti et al, "Ionic Transformations in Extremely Nonpolar Fluorous Media: Phase Transfer Catalysis of Halide Substitution Reactions", Organic Letters, 2007, pp. 2309-2312, vol. 9, No. 12.
Emnet et al, "Syntheses and Properties of Fluorous Quaternary Phosphonium Salts that Bear Four Ponytails; New Candidates for Phase Transfer Catalysts and Ionic Liquids", Adv. Synth. Catal., 2006, pp. 1625-1634, vol. 348.
Bhattacharyya et al., "Phosphorus(III) ligands with fluorous ponytails", J. Chem. Soc., Perkin Trans. 1, 1997, pp. 3609-3612.
Tindale et al., "Highly fluorinated phosphonium ionic liquids: novel media for the generation of superhydrophobic coatings", Chem. Commun., Mar. 6, 2009, pp. 1831-1833.

* cited by examiner

*Primary Examiner* — Brian J Davis
(74) *Attorney, Agent, or Firm* — Hill & Schumacher; Lynn C. Schumacher

(57) ABSTRACT

The present invention provides phosphonium ionic liquids (11) and coatings made therefrom. Highly fluorinated phosphonium ionic liquids based on (11) having been produced exhibiting high thermal stabilities, low melting points and temperature dependent solvent miscibilities. These salts and derivatives of (11) have also been employed in the preparation of superhydrophobic surfaces, indicating that ionic liquids are not only new alternative solvents, but also viable functional materials. All derivatives of (11) form biphasic systems with common laboratory solvents of ranging polarity at room temperature. Based on the solvent miscibility experiments with water and the high fluorine loading, the PILs showed obvious evidence of being hydrophobic. Coatings made with these phosphonium ionic liquids (11), salts and derivatives thereof were superhydrophobic with water contact angles were measured and all of the surfaces were determined to be superhydrophobic with contact angles >150°.

22 Claims, 14 Drawing Sheets

PHOSPHONIUM IONIC LIQUIDS AND COATINGS MADE THEREFROM

CROSS REFERENCE TO RELATED U.S. APPLICATIONS

This patent application is a National Phase application claiming the benefit of PCT/CA2009/000101 filed on Jan. 28, 2009; which further claims the priority benefit from, U.S. Provisional Patent Application Ser. No. 61/006,703 filed on Jan. 28, 2008, in English, entitled PHOSPHONIUM IONIC LIQUIDS AND COATINGS, and which is incorporated herein by reference in its entirety.

FIELD OF THE INVENTION

The present invention relates to phosphonium ionic liquids and coatings made therefrom.

BACKGROUND OF THE INVENTION

Ionic liquids (ILs) are salts composed of distinct organic cation and anion pairs that melt at or below 100° C. Ionic liquids possess remarkable properties, which make them ideal candidates as alternative solvents for synthesis, catalysis and chemical separations (e.g. negligible vapor pressure, high thermal stability, large liquid range) see reference (1). Nitrogen based ILs such as imidazolium (1), ammonium (2) and pyridinium (3) salts are the most widely developed while few reports on sulfonium (4) or phosphonium ionic liquids (5) (PILs) are present in the literature despite their advantages, such as higher thermal stability and increased tolerance towards basic conditions.

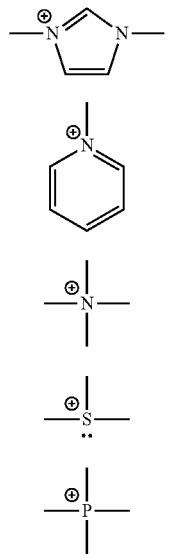

The possible substituents at the cation is highly flexible and when paired with a wide range of potential anions, an extremely large pool of ionic liquids can be generated, all of which contain a variety of properties that can be tuned in order to target certain characteristics, such as melting point, polarity and viscosity to mention just a few. In addition to these more familiar applications, task-specific ionic liquids, containing unusual but potentially useful functionalities, impart these materials with attractive properties not observed in more conventional IL systems. For example, ammonium salts synthesized from natural amino acids (6) produce biodegradable, chiral solvent media, see references (2-6). Catalytically active organometallic complexes can be tethered to ILs, such as the Grubbs Generation I/II catalysts (7), which are highly effective in ring closing olefin metathesis (RCM) with no evidence of catalyst leaching, see reference (7).

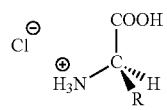

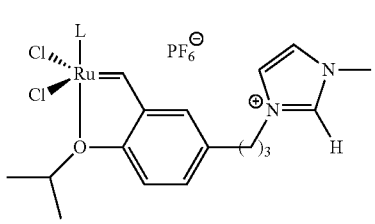

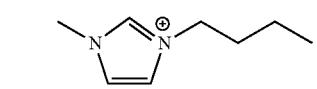

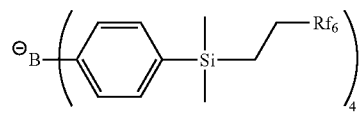

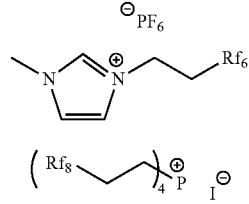

Recently, ionic liquids that contain highly fluorinated substituents appended to either the cation or anion have been reported and utilized as a non-volatile fluorous solvent alternative in fluorous biphasic catalysis (8a), see reference (8) as surfactants for other ionic liquids (8b), see reference (9) and in phase transfer catalysis (8c), see references (10, 11 and 12). Eventually, with intuitive creativity, the concept of structurally manipulating ILs evolved into a paradigm shift in this research field, as these salts are now not only viewed as alternative solvents, but also as novel functionalized materials (e.g. lunar telescope mirror, see reference (11), rewriteable imaging surfaces, see reference (12), lubricants see reference (13), biosensors, see reference (14)).

Ionic liquids have been widely used as solvents for a variety of catalytic methods since they display limited miscibility with organic solvents resulting in a system that allows for efficient catalyst recovery through simple phase separation techniques. However, considering the ionic media does not solubilize apolar organic reagents such as long chain hydrocarbons or neutral metal complexes easily, in some cases, this can result in a decrease in catalytic activity when compared to the traditional homogeneous methods. This limits the application of ionic liquids as solvents for catalysis. In order to improve the solubility of apolar substrates in ionic liquids, an increase in lipophilicity is required.

Introducing fluorinated substituents into the ionic liquid media is one approach to improve the lipophilicity. A further advantage of incorporating perfluorinated substituents is the possibility of generating fluorous biphasic systems (FBSs), see reference (15). This is a temperature dependent separation methodology where the fluorous phase, and an organic phase become miscible at elevated temperatures and then upon cooling, the fluorous and organic layers separate. This concept can be exploited in catalysis. In the two-phase system, a fluorous-tagged catalyst (containing perfluoroalkyl ligands) will selectively partition into the fluorous phase, while the organic substituents will be contained in the organic phase. By increasing the temperature, the system becomes homogenous and the catalysis will proceed. Upon completion of the reaction, the temperature is decreased which initiates phase separation, allowing for isolation of products in the organic layer and recovery of catalyst in the fluorous layer, which can then be recycled.

One drawback to this system is that fluorous solvents are extremely volatile, however, the benefits of homogenous reaction conditions in conjunction with effective product isolation and catalyst recovery are combined into one system. Furthermore, although fluorous solvents display interesting properties and valuable characteristics for many reactions, in some cases, the fluorinated solvent is not capable of forming monophasic solutions at elevated temperatures and therefore does not allow for the reaction to occur with reactants not soluble in the fluorous phase. Strategies to avoid these issues include the utilization of the combined effects of ionic polarity and fluorous properties to enhance selective solubility. This can be achieved by incorporating fluorinated phosphonium ionic liquids as phase transfer catalysts in heterogenous fluorous systems.

A fluorinated silylborate anion $[B\{C_6H_4—(SiMe_2CH_2CH_2C_6F_{13})-p\}_4]$ was paired with a 1-butyl-3-methylimidazolium cation [BMIm] (8a) to generate a solvent media capable of undergoing fluorous biphasic catalyst recycling, see reference (8). The fluorous ionic liquid was insoluble in water and soluble in polar organic solvents and some apolar solvents, in addition to being capable of solubilizing various alkenes and both the non-fluorinated and fluorinated Wilkinson's catalysts. Given these requirements, fluorous biphasic hydrosilylation catalysis was proved to be successful since $[BMIm][B\{C_6H_4—(SiMe_2CH_2CH_2C_6F_{13})-p\}_4]$ formed a homogenous system with the reactants and catalyst at elevated temperatures allowing the reaction to occur and upon cooling and phase separation, resulted in the recovery and subsequent recycling of the catalyst efficiently, even after 15 catalytic cycles. The reaction rate did not surpass the traditional method standards, however, the successful catalyst recovery clearly displayed a significant improvement exhibiting the potential for introducing fluorous biphasic ionic liquid systems for other types of catalysis.

Instead of applying phosphonium ionic liquids as solvents, the salts have been used for phase transfer catalysis, see reference (9). Phase transfer catalysis approach is used when the reactants are located in orthogonal phases. If one of the reactants is a poorly soluble salt the anion can be transported from one phase to the other by interaction with a lipophilic, bulky cation or crown ether, inducing the desired reaction to take place. Fluorinated phosphonium salts (8c) are excellent candidates for phase transfer catalysis since the perfluorinated substituents on the cation or anion are both lipophilic and hydrophobic and could therefore be used in either organic/aqueous, fluorous/organic or fluorous/aqueous biphasic mixtures.

The possibility of undergoing catalysis in fluorous solvents results in a large range of potential reactions to prepare various synthetic targets. Phosphonium salts $[PR_4][A]$ where $R=(CH_2)_2(CF_2)_nCF_3$ where n=5, 7 and A=I, Br, have been applied as phase transfer catalysts for fluorous/aqueous biphasic halide substitution reactions and were recyclable for up to 4 runs.

Another separation technique that involves phosphonium ionic liquids includes using alkyl non-fluorinated phosphonium salts paired with fluorinated imides or phosphates as an extractant for the removal of proteins, protein fragments and/or peptides from biological samples, as disclosed in United States Patent Publication 2007/0026460 A1 (reference 16). The extraction procedure results in the removal of intact proteins that are not degraded and therefore can be thoroughly examined for the presence of disease.

There have been extensive studies on materials that have non-stick surfaces and thus are hydrophobic and oleophobic. Key components of these types of surfaces typically include geometric roughness on the micron to nanoscale and a low free energy coating, see reference (17). Either a rough surface can be prepared and subsequently coated with a hydrophobic substance, or a smooth low free energy material can be prepared and then patterned to generate a coarse surface morphology. The standard method for determining the degree of hydrophobicity of a material involves measuring the contact angle of a liquid droplet, such as water on the surface. If the contact angle is greater than 90° but less than 150° the surface is considered hydrophobic, while if the contact angle is greater than 150° the material is superhydrophobic. Moreover, with increased hydrophobicity, the non-stick properties of the material are superior.

Teflon, a common, commercially available non-stick coating or substance composed of a perfluorinated polymer, polytetrafluoroethylene (PTFE) has a contact angle of 107°. Generally the low free energy materials are perfluorinated molecules, such as Teflon, which with time and heat can release or degrade into toxic volatile compounds. Furthermore, the synthesis of some highly fluorinated polymers involves the generation of toxic volatile compounds such as perfluorocarboxylates (PFCAs), see reference (18).

Therefore a novel material that is superhydrophobic, non-volatile and thermally stable is required in order to improve the current technologies.

SUMMARY OF THE INVENTION

In the present invention, highly fluorinated phosphonium ionic liquids are provided which are capable of forming fluorous biphasic systems and superhydrophobic coatings with water contact angles >150°; an unprecedented application for ionic liquids.

Thus, the present invention provides phosphonium ionic liquids (9),

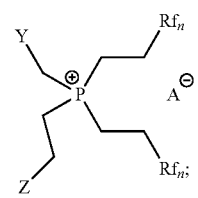

$Rfn = (CF_2)_{n-1}CF_3$ wherein Y is selected from the group consisting of $Rf_n=(CF_2)_{n-1}CF_3$; n=1-25, —$NO_2$, —CN, —OH, —$CF_3$, —COR, —SH, —OMe, —SMe, —SPh, —SSR, —COOH, —COOR, —$NH_2$, —NHR, —$NR_2$, —$Si(OC_2H_5)_3$, $C_2$-$C_{20}$ alkenyl, $C_1$-$C_{20}$ alkoxy, $C_1$-$C_{20}$ alkyl, $C_2$-$C_{20}$ alkynyl, $C_6$-$C_{20}$ alkyl, $C_6$-$C_{12}$ aryl, $C_3$-$C_8$ cycloalkyl, $C_1$-$C_{20}$ aminoalkyl, $C_1$-$C_6$ hydroxyalkyl, $C_1$-$C_{12}$ heteroaryl and $C_1$-$C_{12}$ heterocycle, fluoroalkyl;

wherein Z is selected from the group consisting of —$NO_2$, —CN, —OH, —$CF_3$, —COR, —SH, —OMe, —SMe, —SPh, —COOH, —COOR, —$NH_2$, —NHR, —$NR_2$, $C_2$-$C_{20}$ alkenyl, $C_1$-$C_{20}$ alkoxy, $C_1$-$C_{20}$ alkyl, $C_2$-$C_{20}$ alkynyl, $C_6$-$C_{20}$ alkyl, $C_6$-$C_{12}$ aryl, $C_3$-$C_8$ cycloalkyl, $C_1$-$C_{20}$ aminoalkyl, $C_1$-$C_6$ hydroxyalkyl, $C_1$-$C_{12}$ heteroaryl and $C_1$-$C_{12}$ heterocycle; and wherein A is selected from the group consisting of $F^-$, $Cl^-$, $Br^-$, $I^-$, $ClO_4^-$, $PF_6^-$, $N_3^-$, $BF_4^-$, $SbF_6^-$, $BH_4^-$, $(FSO_2)_2N^-$, $(CF_3SO_2)_2N^-$, $(C_2F_5SO_2)_2N^-$, $(CF_3SO_2)_3C^-$, $CF_3SO_3$, $ROSO_3^-$, $CF_3COO^-$, $AsF_6^-$, $RCOO^-$, $(CN)_2N^-$, and $NO_3^-$ and $MePhO_2SO^-$.

When Y=$C_2$-$C_{20}$ alkyl chain, there may be included a crosslinkable group bonded to a terminal carbon of the $C_2$-$C_{20}$ alkyl chain which may be any one of acrylate, methacrylate, norbornadienyl, styrenyl, alkenyl, alkynyl, maleimidyl and anthracenyl. Similarly a polymerizable group may be bonded to the terminal carbon of the $C_2$-$C_{20}$ alkyl chain which may be any one of acrylate, methacrylate, norbornadienyl, styrenyl, alkenyl, alkynyl, maleimidyl, [1]metalloarenophanyl and [2]metalloarenophanyl to give some non-limiting examples. The phosphonium ionic liquids (11) with the crosslinkable groups or polymerizable groups may be polymerized to form a solid polymer. These polymerized phonphonium ionic liquids may then be cast into films, shapes or coatings.

When Y=$C_2$-$C_{20}$ alkyl chain, there may be included a group bonded to a terminal carbon of the $C_2$-$C_{20}$ alkyl chain with the group being any one of —$NO_2$, —CN, —OH, —$CF_3$, —COR, —SH, —OMe, —SMe, —SPh, —SSR, —COOH, —COOR, —$NH_2$, —NHR, —$NR_2$, $C_2$-$C_{20}$ alkenyl, $C_1$-$C_{20}$ alkoxy, $C_1$-$C_{20}$ alkyl, $C_2$-$C_{20}$ alkynyl, $C_6$-$C_{20}$ alkyl, $C_6$-$C_{12}$ aryl, $C_3$-$C_8$ cycloalkyl, $C_1$-$C_{20}$ aminoalkyl, $C_1$-$C_6$ hydroxyalkyl, $C_1$-$C_{12}$ heteroaryl and $C_1$-$C_{12}$ heterocycle, and fluoroalkyl to give some non-limiting examples.

A further understanding of the functional and advantageous aspects of the invention can be realized by reference to the following detailed description and drawings.

BRIEF DESCRIPTION OF THE DRAWINGS

Embodiments of the present invention are described in greater detail with reference to the accompanying drawings in which.

DETAILED DESCRIPTION OF THE INVENTION

Figure 1:
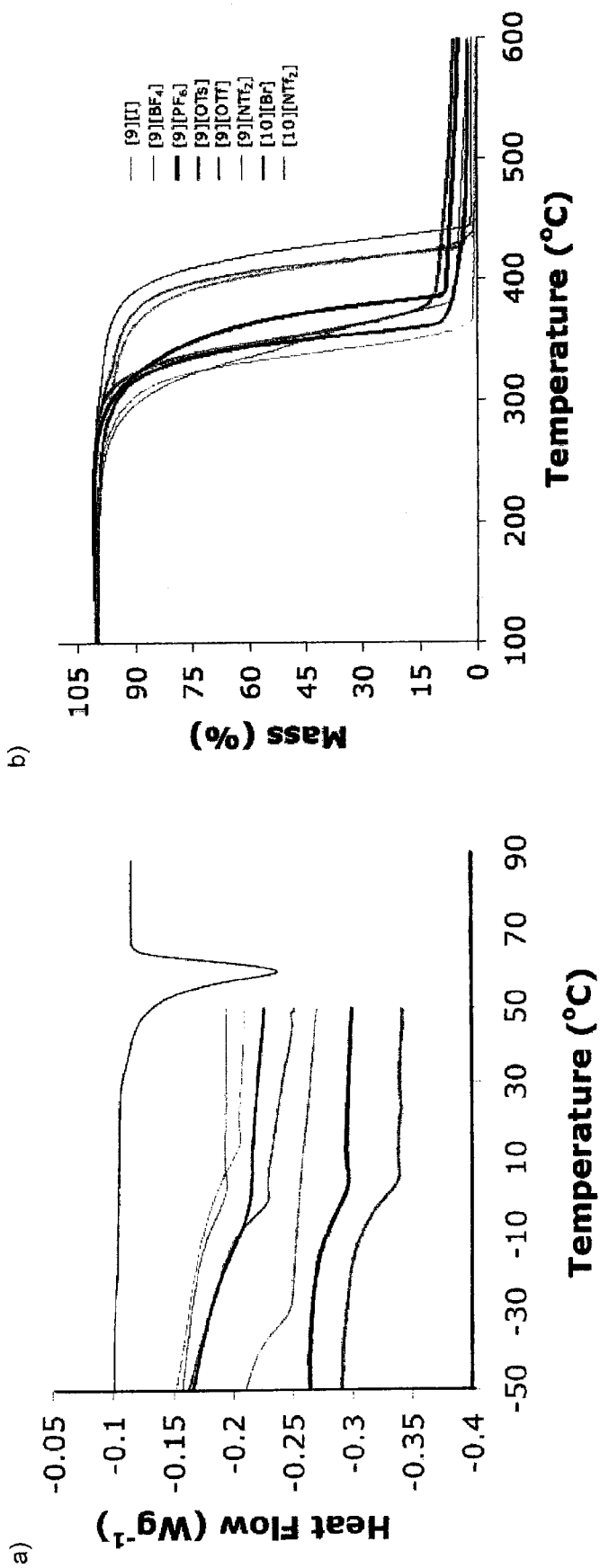
FIG. 1a) shows the DSC (Differential Scanning Calorimetry) curves for six (6) [9][A] ionic liquids and two (2) [10][A] liquids identified in the legend of the Figure, which display glass transitions for the liquids and b) shows the TGA curves demonstrating the decomposition data for these ionic liquids.

Generally speaking, the systems described herein are directed to phosphonium ionic liquids and coatings made therefrom. As required, embodiments of the present invention are disclosed herein. However, the disclosed embodiments are merely exemplary, and it should be understood that the invention may be embodied in many various and alternative forms. The Figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present invention. For purposes of teaching and not limitation, the illustrated embodiments are directed to phosphonium ionic liquids and coatings made there from.

As used herein, the term "about", when used in conjunction with ranges of dimensions, temperatures or other physical properties or characteristics is meant to cover slight variations that may exist in the upper and lower limits of the ranges of dimensions so as to not exclude embodiments where on average most of the dimensions are satisfied but where statistically dimensions may exist outside this region.

The present invention provides methods for the synthesis and characterisation of a two exemplary series (9 and 10) of a broader novel class of highly fluorinated phosphonium ionic liquids (PILs) (11), where these materials are low melting, thermally stable and exhibit selective temperature dependent solvent miscibilities. The phosphonium ionic liquids (11) has the following structure.

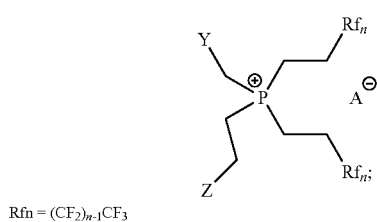

$Rf_n = (CF_2)_{n-1}CF_3$

Y may be any one of $Rf_n=(CF_2)_{n-1}CF_3$; n=1-25, —$NO_2$, —CN, —OH, —$CF_3$, —COR, —SH, —OMe, —SMe, —SPh, —SSR, —COOH, —COOR, —$NH_2$, —NHR, —$NR_2$, —$Si(OC_2H_5)_3$, $C_2$-$C_{20}$ alkenyl, $C_1$-$C_{20}$ alkoxy, $C_1$-$C_{20}$ alkyl, $C_2$-$C_{20}$ alkynyl, $C_6$-$C_{20}$ alkyl, $C_6$-$C_{12}$ aryl, $C_3$-$C_8$ cycloalkyl, $C_1$-$C_{20}$ aminoalkyl, $C_1$-$C_6$ hydroxyalkyl, $C_1$-$C_{12}$ heteroaryl and $C_1$-$C_{12}$ heterocycle and fluoroalkyl to give some non-limiting examples.

Z may be any one of —$NO_2$, —CN, —OH, —$CF_3$, —COR, —SH, —OMe, —SMe, —SPh, —COOH, —COOR, —$NH_2$, —NHR, —$NR_2$, $C_2$-$C_{20}$ alkenyl, $C_1$-$C_{20}$ alkoxy, $C_1$-$C_{20}$ alkyl, $C_2$-$C_{20}$ alkynyl, $C_6$-$C_{20}$ alkyl, $C_6$-$C_{12}$ aryl, $C_3$-$C_8$ cycloalkyl, $C_1$-$C_{20}$ aminoalkyl, $C_1$-$C_6$ hydroxyalkyl, $C_1$-$C_{12}$ heteroaryl and $C_1$-$C_{12}$ heterocycle.

The anion A may be any one of $F^-$, $Cl^-$, $Br^-$, $I^-$, $ClO_4^-$, $PF_6^-$, $N_3^-$, $BF_4^-$, $SbF_6^-$, $BH^-$, $(FSO_2)_2N^-$, $(CF_3SO_2)_2N^-$, $(C_2F_6SO_2)_2N^-$, $(CF_3SO_2)_3C^-$, $CF_3SO_3^-$, $ROSO_3^-$, $CF_3COO^-$, $AsF_6^-$, $RCOO^-$, $(CN)_2N^-$, and $NO_3^-$ and $MePhO_2SO^-$ to give some non-limiting examples.

In an embodiment of the phosphonium ionic liquid (11) when Z=$Rf_n$ then Y is not $Rf_n$ and not fluoroalkyl.

In another embodiment, when Y=$C_2$-$C_{20}$ alkyl chain, there may be included a crosslinkable group bonded to a terminal carbon of the $C_2$-$C_{20}$ alkyl chain which may be any one of acrylate, methacrylate, norbornadienyl, styrenyl, alkenyl, alkynyl, maleimidyl and anthracenyl. Similarly a polymerizable group may be bonded to the terminal carbon of the $C_2$-$C_{20}$ alkyl chain which may be any one of acrylate, methacrylate, norbornadienyl, styrenyl, alkenyl, alkynyl, maleimidyl, [1]metalloarenophanyl and [2]metalloarenophanyl to give some non-limiting examples. The phosphonium ionic liquids (11) with the crosslinkable groups or polymerizable groups may be polymerized to form a solid polymer. These polymerized phonphonium ionic liquids may then be cast into films, shapes or coatings.

In other embodiments of the phosphonium ionic liquid (11) when Y=$C_2$-$C_{20}$ alkyl chain, there may be included a group bonded to a terminal carbon of the $C_2$-$C_{20}$ alkyl chain with the group being any one of —$NO_2$, —CN, —OH, —$CF_3$, —COR, —SH, —OMe, —SMe, —SPh, —SSR, —COOH, —COOR, —$NH_2$, —NHR, —$NR_2$, —$Si(OC_2H_5)_3$, $C_2$-$C_{20}$ alkenyl, $C_1$-$C_{20}$ alkoxy, $C_1$-$C_{20}$ alkyl, $C_2$-$C_{20}$ alkynyl, $C_6$-$C_{20}$ alkyl, $C_6$-$C_{12}$ aryl, $C_3$-$C_8$ cycloalkyl, $C_1$-$C_{20}$ aminoalkyl, $C_1$-$C_6$ hydroxyalkyl, $C_1$-$C_{12}$ heteroaryl and $C_1$-$C_{12}$ heterocycle, and fluoralkyl to give some non-limiting examples.

The phosphonium ionic liquids (11) may be mixed with an organic solvent to form a fluorous biphasic system. Non-limiting examples of organic solvents include tetrahydrafurane (THF), $CH_2Cl_2$, toluene, benzene, $CHCl_3$, hexane, pentane and acetonitrile to mention a few non-limiting examples.

These phosphonium ionic liquids (11) may be applied to a surface of a substrate as one of a hydrophobic or a superhydrophobic coating on the surface.

The phosphonium ionic liquids (11) may be applied to surfaces of metals, polymers, semiconductors, crystalline surfaces, ceramics and glasses to mention just a few. Common metals to which these coatings may be applied include, but are not limited to, copper, silver, gold, aluminum, indium, chromium, steel, iron, cobalt, stainless steel, titanium, vanadium, and alloys thereof. Common polymers to which the coatings may be applied include polyethylene, polyacrylate, polystyrene just to mention a few non-limiting examples.

These phosphonium ionic liquids can be applied to surfaces for use as an antistatic coating or as a water vapour barrier coating. For example, as water vapour barriers the phosphonium ionic liquids can be applied to a surface of an organic light emitting diode or a solar cell. These coatings may be used as barrier coatings to bulk water as well, aqueous solutions, biological liquids such as blood, urine, saliva etc. The phosphonium ionic liquids may be applied to nanoparticles, whether metal, semiconducting, inorganic or polymer nanoparticles to mention just a few.

These phosphonium ionic liquids (11) may be applied to a surface of a substrate as one of a hydrophobic or a superhydrophobic coating on the surface.

Through the selective depositing or removal of hydrophobic or superhydrophobic coating (or polymer or coated surface-bound nanoparticle), patterned surfaces with alternating (super) hydrophobic and hydrophilic regions can be created on a nano- or micro-scale. Selective removal techniques may include; sputtering, electron beam lithography (e-beam lithography), focused ion beam (FIB) lithography, or atomic force microscopy (ATM) lithography. The purpose is to create very small structures in the top layer of the coating or polymer that can subsequently find uses in the creation of microelectronic devices, microfluidic channels, microarrays, biosensors, lab-on-a-chip devices and inkjet printers.

For purposes of illustration only, and not to limit or restrict the invention in any way, the following gives example methods for producing two series of phosphonium salts, (9 and 10) with varied fluorine loadings and the resulting structural and chemical properties illustrating the utility of these ionic liquids as hydrophobic and superhydrophobic coatings.

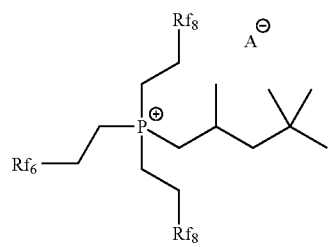

A = I, $PF_6$, $BF_4$, $NTf_2$, OTf, OTs

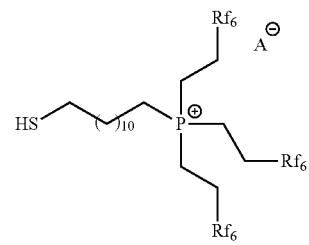

A = Br, $NTf_2$

A modular synthetic approach was employed to generate several series of phosphonium salts with varied fluorine loadings. Series 9 involved the synthesis of a fluorinated alkyl phosphine, $RP[(CH_2)_2Rf_8]_2$ (R=2,4,4'-trimethylpentyl; $Rf_8$=$(CF_2)_7CF_3$) by the radical addition of $RPH_2$ to a fluorous olefin followed by the quaternization of the fluorinated phosphine with a fluorous iodide, I(CH$_2$)$_2$Rf$_6$, resulting in a viscous, fluorinated phosphonium iodide ionic liquid, [9][I] see reference (19).

Although members from series 9 exhibit superhydrophobic coatings properties, these highly fluorinated phosphonium ionic liquids physisorb to a surface. Therefore, in order to generate films of greater resiliency and adhesion, modifications to the general synthetic strategy were employed to produce series (10). Incorporating a pendant thiol functionality into the cation targets a covalent linkage to Ag substrates, instilling enhanced retention of the superhydrophobic coating on the surface and resulting in a more durable film. To produce such a material, a highly fluorinated phosphine, P[(CH$_2$)$_2$Rf$_6$]$_3$ was prepared and reacted with a 1-bromododedecylthiol to generate a highly fluorinated phosphonium salt ([10][Br]) with an appended thiol, see references (20) and (21).

It is well established that tuning the melting point and other physical properties of ionic liquids can be achieved by exchanging the cation-anion pair. Therefore a variety of counter anions have been incorporated via metathetical routes giving the corresponding salts [9][BF$_4$], [9][PF$_6$], [9][OTs], [9][OTf] and [9][NTf$_2$] (OTs=tosylate; OTf=trifluoromethanesulfonate (triflate); NTf$_2$=bistrifluoromethanesulfonimide).

EXPERIMENTAL SECTION

The 2,4,4'-trimethylpentyl phosphine was obtained from Cytec Corporation. Silver p-toluenesulfonate AgOTs (Aldrich), TMS-OTf, AgBF$_4$, AgPF$_6$ (Alfa Aesar), LiNTf$_2$ (Fluka), AgNO$_3$ (EMD), 1H,1H,2H-perfluorodec-1-ene, 1H,1H,2H,2H-perfluorooctyliodide (Fluorous Technologies Inc.) and VAZO 67, 2,2'-azobis(2-methylbutanenitrile) (Dupont) were used as received without further purification. The purity of all reagents was assessed by multinuclear NMR spectroscopy ($^1$H, $^{19}$F{$^1$H}, $^{31}$P{$^1$H}), and they were stored in a nitrogen-filled MBraun Labmaster 130 glove box. Solvents were obtained from Caledon Laboratories and dried using an Innovative Technologies Inc. Solvent Purification System. The dried solvents were collected under vacuum and stored under a nitrogen or argon atmosphere in Strauss flasks, or stored in the drybox over 4 Å molecular sieves. Deuterated chloroform was dried with CaH$_2$, vacuum distilled and stored over 4 Å molecular sieves in the glove box. Solution $^1$H, $^{31}$P{$^1$H} and $^{19}$F{$^1$H} NMR spectra were recorded on a Varian INOVA 400 MHz spectrometer unless otherwise noted ($^1$H, 400.09 MHz, $^{31}$P; 161.82 MHz, $^{19}$F; 376.15 MHz). All samples for $^1$H NMR spectroscopy were referenced to the residual protons in the solvent relative to (CH$_3$)$_4$Si (δ (ppm); chloroform-d 7.26; acetone-d$_6$ 2.05). Phosphorus-31 and $^{19}$F NMR chemical shifts were reported relative to external standards (85% H$_3$PO$_4$; 0.00 ppm and CF$_3$(C$_6$H$_5$); -63.9 ppm, relative to CFCl$_3$; 0.00 ppm). Mass spectrometry measurements were recorded in positive and negative ion modes using an electrospray ionization Micromass LCT spectrometer. Elemental analyses were performed by Guelph Chemical Laboratories Ltd., Guelph, Ontario, Canada and Columbia Analytical Services Inc., Tucson, Ariz., USA.

The decomposition temperatures were determined using Thermal Gravimetric Analysis (TGA) on a TGA/SDTA 851e Mettler Toledo instrument for series (9) or on a Q600 SDT TA Instrument for series (10). A 0.005-0.010 g sample was heated at a rate of 10° C./min over a temperature range of 100° C.-600° C. Isothermal heating experiments were conducted using a 0.005-0.010 g sample of the PIL heated at 120° C. for 5 h for series (9) and at 180° C. for 10 h for [10][Br] and the percent mass loss was determined using Thermal Gravimetric Analysis. Melting and glass transition points were determined using Differential Scanning Calorimetry (DSC) on a DSC 822$^e$ Mettler Toledo instrument for series (9) or on a Q20 DSC TA instrument for series (10). For series (9) a 0.005 g-0.010 g sample was cooled to -70° C. where the temperature was sustained for 15 minutes, followed by heating to 500° C. at 10° C./min. For series (10) a 0.005 g-0.010 g sample was cooled -90° C. and then heated to 200° C. at 10° C./min, cooled to -90 at 10° C./min and finally reheated to 200° C. at 10° C./min. The glass transition temperatures were taken from the final heat cycle. All thermal analysis experiments were conducted in a N$_{2\,(g)}$ atmosphere.

The phosphonium ionic liquids were tested for their water content by Karl Fischer titration, on a 684 KF Coulometer by Metrohm. The samples were first dried in vacuo for 3 h at 100° C., transferred to a glove box, where they were weighed out (0.02 g), and dissolved in dry CH$_2$Cl$_2$. The water content of the CH$_2$Cl$_2$ was determined, and was subtracted from the value obtained for each ionic liquid. The microsyringe was cleaned and dried between each titration.

The conductivity of the ionic liquids was obtained using the complex impedance method, which employs measurement of the cell impedance as a function of AC potential frequency ranging from 10 kHz to 10$^{-2}$ Hz. The conductivity cell was made of two parallel gold-plated electrodes with a cell constant, l/A=13.0 cm$^{-1}$, that was calibrated with standard solutions of KCl. The impedance data were collected using a Solartron model 1240 potentiostat and 1252 frequency response analyzer. The impedance of the ionic liquid arises from resistive (R) and capacitive (C) contributions, and can be described by Z=Z$_{real}$+jZ$_{im}$=R+j/ωC where ω is the frequency of the AC potential. The impedance data were plotted in a Nyquist Plot (imaginary vs. real impedance) and the real impedance value at the low frequency limit was used to obtain the conductivity, κ, where κ=(1/R)·(l/A).

The miscibility of THF in the fluorous ionic liquids was determined by adding THF (0.5 mL) to a sample of the ionic liquid (0.331-0.430 g). The biphasic mixture was stirred at 65° C. until the solution became monophasic and then was allowed to cool to RT followed by further cooling to -30° C. overnight. An alloquot of the THF layer (0.1 mL) was removed upon separation of THF and PIL at RT and again at -30° C. The THF was removed in vacuo, the remaining PIL was weighed and the ratio of the mass remaining to the initial mass was determined as the amount of contamination of PIL in the THF phase.

To prepare the superhydrophobic surfaces, a copper plate (15 mm×15 mm×2 mm) was cleaned using a polishing wheel (4000 grit sand paper) and then washed with acetone and EtOH and dried under stream of N$_{2\,(g)}$. A silver coating was deposited on the surface by immersing the copper plate in a 0.01 M AgNO$_3$ solution for 2 min. The plate was dried under a stream of N$_{2\,(g)}$ and re-immersed in the AgNO$_3$ for 5 min, dried, re-immersed for a further 5 min and then dried. The Ag-coated copper plate was then dip coated (50 times) into a solution of [9][A] in acetone (8.15 mmol·L$^{-1}$) and for [10][A] the substrate was immersed in solution of acetone (8.15 mmol·L$^{-1}$) for 15 min. Scanning electron microscope images of the surfaces were obtained using a Hitachi S-4500 instrument, operated at an electron beam voltage of 5 kV or the LEO/Zeiss 1540XB FIB/SEM CrossBeam operated at an electron beam voltage of 1 kV. Water contact angles were measured on a Ramé-Hart Instrument Co. goniometer with DROPimage software or on a FTA 1000 Drop Shape Instrument, B Frame with FTA Video Drop Shape Software. Using an automated dispensing system, a minimum of 3 static 4-6

μL droplets of ultrapure water (Aldrich) were deposited in different areas upon the surface. The contact angles were measured and repeated on at least 3 identical substrates and the results were averaged.

Methodologies for synthesizing the phosphine precursors have been previously reported, however, numerous modifications to the procedures are included.

Synthesis of $C(CH_3)_3CH_2CH(CH_3)CH_2P((CH_2)Rf_8)_2$, See Reference (19).

A (15 mL) pressure tube was charged with 1H,1H,2H-perfluorodec-1-ene (23.8 mmol), 2,4,4'-trimethylpentyl phosphine, 40 wt % in toluene, (11.9 mmol) and VAZO 67 (0.95 mmol, 8 mol %) under nitrogen and stirred at 80° C. for 2 h. Further addition of VAZO 67 was added every 2 h (3×8 mol %), after which, the solution was stirred at 80° C. for 17 h. Excess fluorous olefin, and diethyldimethyl-succinonitrile were removed via sublimation from the oil (60° C.; –20° C. cold finger). The remaining brown liquid was distilled (0.05 mmHg, 140° C.) to give a colourless viscous liquid (8.67 g, 8.35 mmol, 70%). $^1H$ NMR (399.76 MHz, $CDCl_3$) δ (ppm); 2.23-2.08 (m, 4H, $PCH_2CH_2$), 1.67-1.57 (m, 5H, $PCH_2CH_2$ and $(CH_3)_3CH_aH_bCHCH_3)$), 1.51-1.45 (ddd, 1H, $(CH_3)_3CH_aH_bCHCH_3$), $^2J$=14.0 Hz, $^3J$=3.2 Hz), 1.39-1.31 (m, 2H, $(CH_3)_3CH_aH_bCHCH_3CH_2P)$), 1.20-1.14 (ddd, 1H, $(CH_3)_3CH_aH_bCHCH_3$), $^2J$=14.0 Hz, $^3J$=1.2 Hz), 1.07-1.05 (d, 3H, $(CH_3)_3CH_aH_bCHCH_3$, J=6.8 Hz), 0.89 (s, 9H$(CH_3)_3CH_aH_bCHCH_3$)); $^{19}F\{^1H\}$ NMR (376.15 MHz, $CDCl_3$) δ (ppm); –86.6 (m, 6F), –120.6 (m, 4F), –127.6 (m, 12F), –128.5 (m, 4F), –129.1 (m, 4F), –131.9 (m, 4F); $^{31}P\{^1H\}$ NMR (161.83 MHz, $CDCl_3$) δ (ppm); –31.5 (s). MS (ESI); m/z$^+$ (%): 1037.1 (100) [M$^+$].

Figure 12:
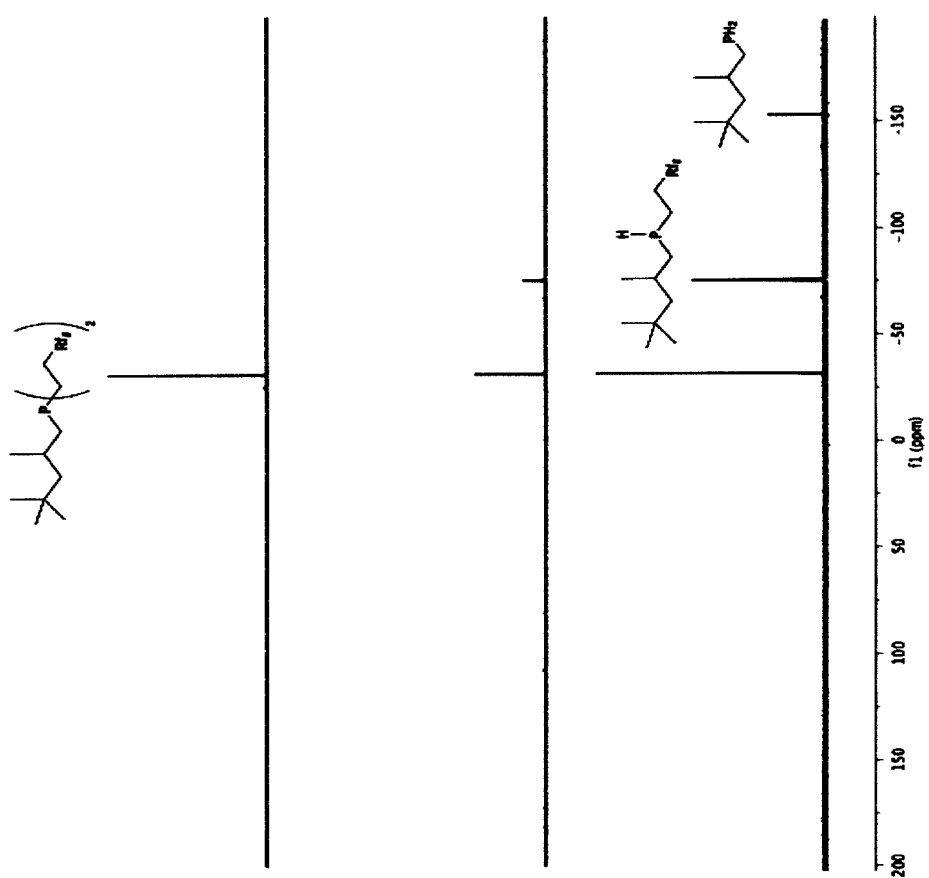
FIG. 12 shows the $^{31}P\{^1H\}$ NMR spectrum indicating the transition from the primary phosphine to the fluorinated tertiary phosphine.
Figure 13:
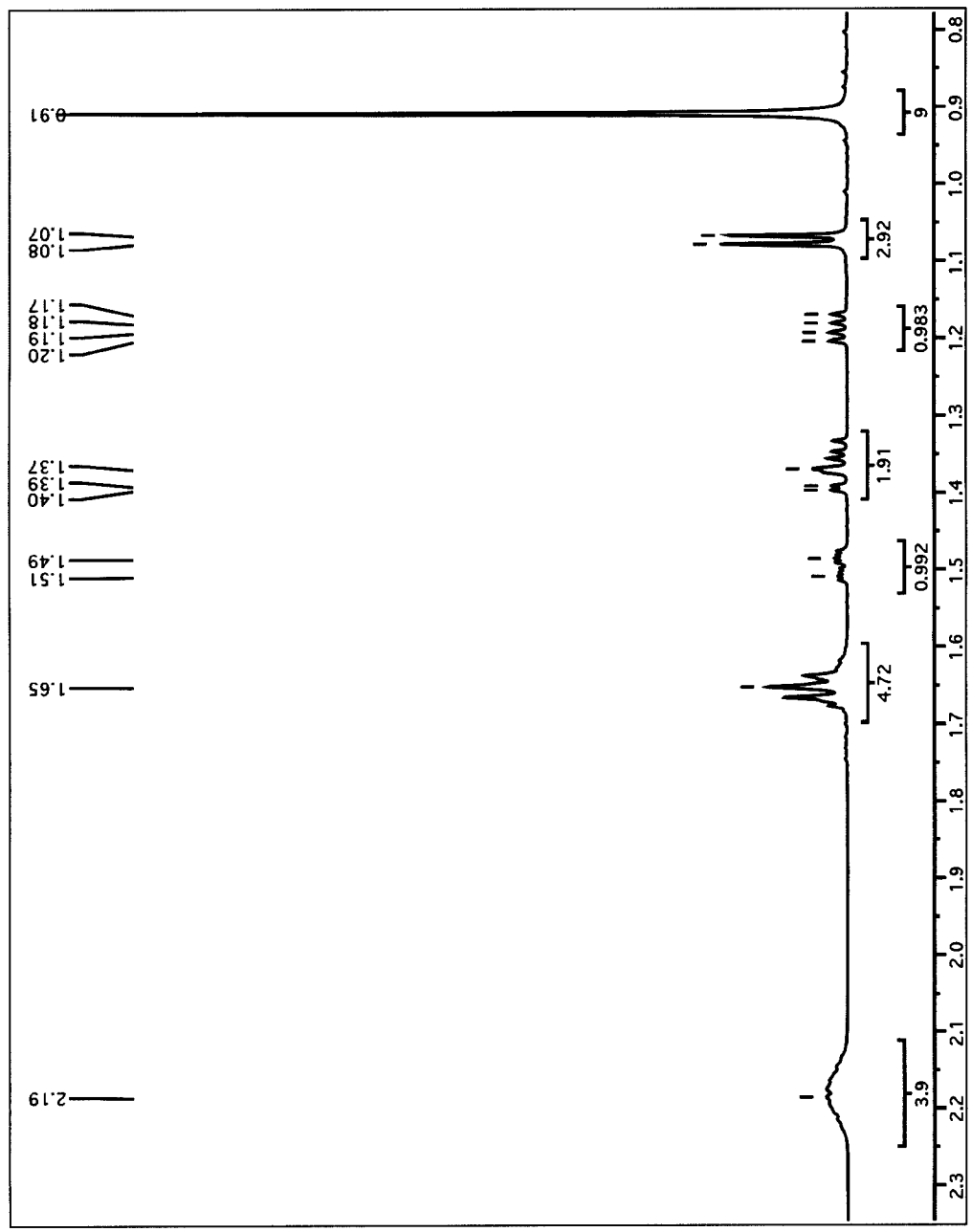
FIG. 13 shows the $^1H$ NMR spectrum of the fluorous phosphine.

FIG. 12 shows the $^{31}P\{H\}$ NMR spectrum indicating the transition from the primary phosphine to the fluorinated tertiary phosphine. FIG. 13 shows the $^1H$ NMR spectrum of the fluorous phosphine.

Synthesis of [9][I]

A 100 mL round bottom schlenk flask was charged with $RP[(CH_2)_2Rf_8]_2$ (R=2,4,4'-trimethylpentyl)(2.663 g, 2.570 mmol), $I(CH_2)_2Rf_6$ (2.432 g, 5.131 mmol) and DMF (5 mL). The solution was heated to 120° C. and stirred for 6 h under a flow of nitrogen. The DMF was removed in vacuo (0.05 mmHg, 100° C.). The resulting liquid was dissolved in a minimal amount of acetone and extracted with 1:5 n-pentane: toluene mixture and placed at –30° C. to promote separation of product. Excess solvent was decanted and the residual volatiles were removed in vacuo resulting in a clear yellow glassy liquid (3.566 g, 2.358 mmol, 92%). $^1H$ NMR (399.76 MHz, Acetone-$d_6$) δ (ppm); 3.45-3.38 (m, 6H, $PCH_2CH_2$), 3.23-3.18 (dd, 2H, $(CH_3)_3CH_aH_bCHCH_3CH_2P$), $^2J$=13.6 Hz, $^3J$=6.4), 3.11-2.96 (m, 6H, $PCH_2CH_2$), 2.47-2.40 (m, 1H, $(CH_3)_3CH_aH_bCHCH_3$)), 1.63-1.59 (dd, 1H, $(CH_3)_3CH_aH_b$-$CHCH_3$), $^2J$=14.0 Hz, $^3J$=2.4 Hz), 1.49-1.44 (dd, 1H, $(CH_3)_3CH_aH_bCHCH_3$), $^2J$=14.0 Hz, $^3J$=8.4 Hz), 1.33-1.31 (d, 3H, $(CH_3)_3CH_aH_bCHCH_3$, J=6.8 Hz), 0.97 (s, 9H, $(CH_3)_3CH_aH_bCHCH_3$)); $^{19}F\{^1H\}$ NMR (376.15 MHz, Acetone-$d_6$) δ (ppm); –82.2 (m, 9F), –115.4 (m, 6F), –122.9 (m, 14F), –123.8 (m, 12F), –127.3 (m, 6F); $^{31}P\{^1H\}$ NMR (161.83 MHz, Acetone-$d_6$) δ (ppm); 40.3 (s). MS (ESI); mz$^+$ (%): 1385.0 (100) [M$^+$-I], 2897.4 (20) [M$_2$I$^+$], 3151.6 (10) [M$_3$I$_2^+$].

Figure 14:
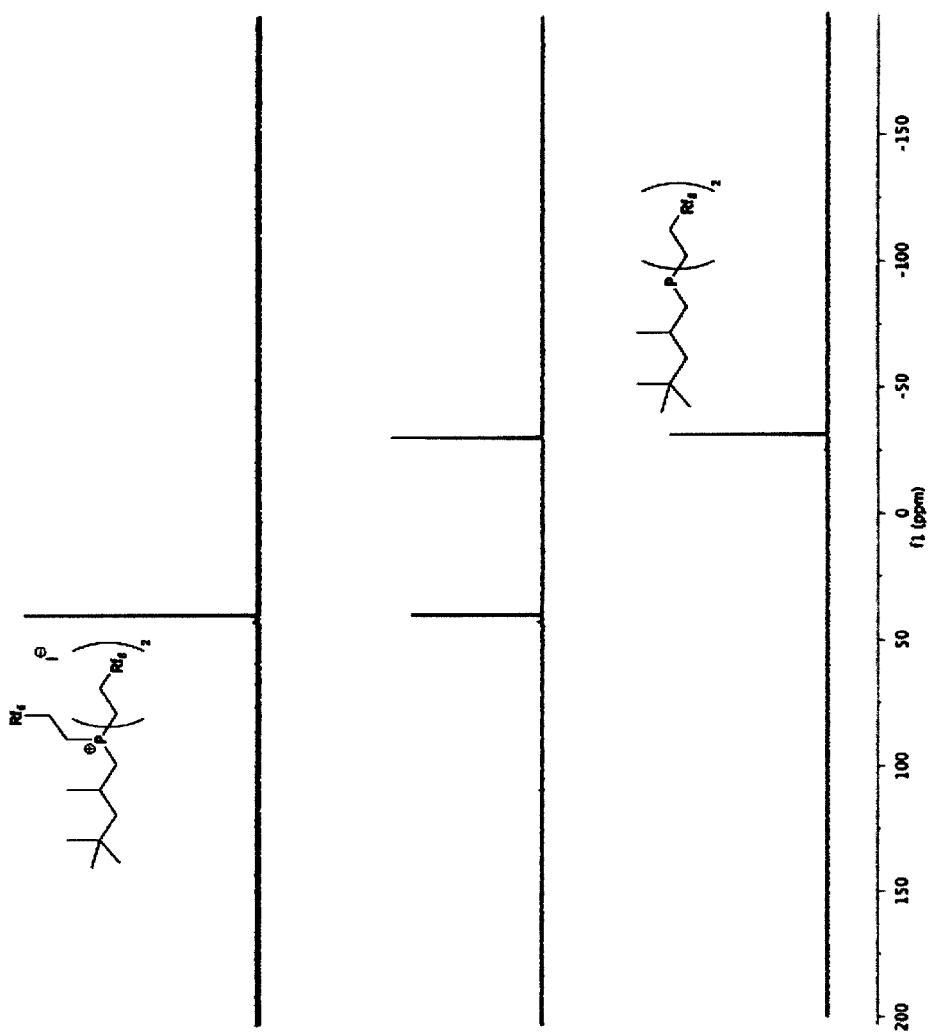
FIG. 14 shows the $^{31}P\{^1H\}$ NMR spectrum demonstrating the conversion of the phosphine to the phosphonium salt [9][OTs]

FIG. 14 shows the $^{31}P\{^1H\}$ NMR spectrum demonstrating the conversion of the phosphine to the phosphonium salt [9][I].

General Procedure for Anion Exchange Reactions for [9] [BF$_4$] [9][PF$_6$] and [9][OTs].

A vial wrapped in aluminum foil was charged with the desired silver salt (AgBF$_4$, AgPF$_6$ or AgOTs, 2.49 mmol) in trifluorotoluene (5 mL). The phosphonium iodide (1.66 mmol) in trifluorotoluene (40 mL) was heated to dissolve (80° C.), added to the silver salt mixture and stirred for 5 days. The resulting suspension was centrifuged, the supernatant was passed through a celite column and the volites were removed in vacuo, yielding the desired phosphonium salt as a yellow viscous liquid. [9][BF$_4$]; 0.73 g, 0.50 mmol, 75%; MS (ESI); m/z$^{+/-}$ (%): 1384.8 (100) [M$^+$-BF$_4$], 2857.1 (2) [M$_2$BF$_4^+$], 1557.4 (100) [M(BF$_4$)$_2^-$], 3029.9 (15) [M$_2$(BF$_4$)$_3^-$]; Anal. Calcd. (Found) C, 29.35 (29.39); H, 1.99 (1.76). [9][PF$_6$]; 1.58 g, 1.04 mmol, 74%; MS (ESI); m/z$^{+/-}$ (%): 1387.3 (100) [M$^+$-PF$_6$], 2913.2 (35) [M$_2$PF$_6^+$], 1674.2 (100) [MPF$_6^-$], 3205.3 (10) [M$_2$(PF$_6$)$_3$–]; Anal. Calcd. (Found) C, 28.23 (29.16); H, 1.91 (1.79). [9][OTs; 2.09 g, 1.34 mmol, 98%; MS (ESI); m/z$^{+/-}$ (%): 1384.9 (100) [M$^+$-OTs], 2941.1 (38) [M$_2$OTs$^+$], 1726.9 (100) [MOTs$_2$], 3284.1 (18) [M$_2$OTs$_3^-$]; Anal. Calcd. (Found) C, 33.16 (33.31); H, 2.33 (2.58).

Synthesis of [9][OTf].

[9][I] (0.2 g, 0.132 mmol) and trifluorotoluene (4 mL) and were heated (80° C.) until monophasic. Trimethylsilyltriflate (0.044 g, 0.198 mmol) in trifluorotoluene (1 mL) was added and the solution was stirred at RT for 18 h, at which time the volatiles were removed in vacuo, resulting in viscous yellow liquid (0.15 g, 0.10 mmol, 75%). MS (ESI); m/z$^{+/-}$ (%): 1384.9 (100) [M$^+$-OTf], 2919.5 (5) [M$_2$OTf$^+$], 1683.0 (100) [MOTf$_2^-$], 3217.8 (35) [M$_2$OTf$_3^-$]; Anal. Calcd. (Found) C, 28.94 (29.16); H, 1.91 (2.15).

Synthesis of [9][NTf$_2$].

[9][I] (0.65 g, 0.43 mmol) and acetone (4 mL) and were heated (80° C.) until monophasic. Lithium bistriflimide (0.19 g, 0.65 mmol) in acetone (1 mL) was added and the solution was stirred at RT for 48 h. The solvent was removed in vacuo and the resulting yellow liquid was dissolved in trifluorotoluene and filtered. The filtrate was extracted with H$_2$O (20 mL×4) and each aqueous layer was titrated with 10% AgNO$_3$ solution to confirm the removal of LiI. The organic fraction was dried with MgSO$_4$ and the volatiles were removed in vacuo producing a yellow waxy solid (0.55 g, 0.33 mmol, 76%).

[9][NTf$_2$]: MS (ESI); m/z$^{+/-}$ (%): 1387.4 (100) [M$^+$-(NTf$_2$)$^+$)], 3048.3 (35) [M$_2$(NTf$_2$)$^+$], 1944.2 (70) [M(NTf$_2$)$_2^-$], 3610.8 (15) [M$_2$(NTf$_2$)$_3^-$].

Note: The $^{31}P\{^1H\}$ NMR spectra for the anion exchange products were identical to the phosphonium iodide (40.3 ppm). The anion exchange $^1H$ NMR and $^{19}F\{^1H\}$ NMR spectra were identical, given the nature of the alkyl and fluorous alkyl chains with the obvious variations for the specific anion.

General [9][A]:

$^1H$ NMR (399.76 MHz, Acetone-$d_6$) δ (ppm); 3.30-3.23 (m, 6H, PCH$_2$CH$_2$), 3.08-2.94 (m, 8H, PCH$_2$CH$_2$, $(CH_3)_3CH_aH_bCHCH_3CH_2P$)), 2.45-2.34 (m, 1H, $(CH_3)_3CH_aH_bCHCH_3$)), 1.56-1.45 (m, 2H, $(CH_3)_3CH_aH_b$-CHCH$_3$), 1.31 (d, 3H, $(CH_3)_3CH_aH_bCHCH_3$, J=8.0 Hz), 0.96 (s, 9H, $(CH_3)_3CH_aH_bCHCH_3$)).

General [9][A]:

$^{19}F\{^1H\}$ NMR (376.15 MHz, Acetone-$d_6$) δ (ppm); –81.6 (t, 9F, $^3J_{F-F}$=9.9 Hz), –115.5 (m, 6F), –122.5 (m, 14F), –123.6 (m, 12F), –127.1 (m, 6F).

[9][BF$_4$]:

$^{19}F\{^1H\}$ NMR (376.15 MHz, Acetone-$d_6$) δ (ppm); –149.2 (s, 4F, $^1J_{B-F}$=19.5 Hz)

[9][PF$_6$]:

$^{19}F\{^1H\}$ NMR (376.15 MHz, Acetone-$d_6$) δ (ppm); –72.8 (d, 6F, $^1J_{P-F}$=708.3 Hz); $^{31}P\{^1H\}$ NMR (161.83 MHz, Acetone-$d_6$) δ (ppm); –142.8 (sept, 6F, $^1J_{P-F}$=708.2 Hz)

[9][OTs]:

$^1$H NMR (399.76 MHz, Acetone-d$_6$) δ (ppm); 7.67 (d, 2H), 7.12 (d, 2H), 2.31 (s, 3H).

Figure 15:
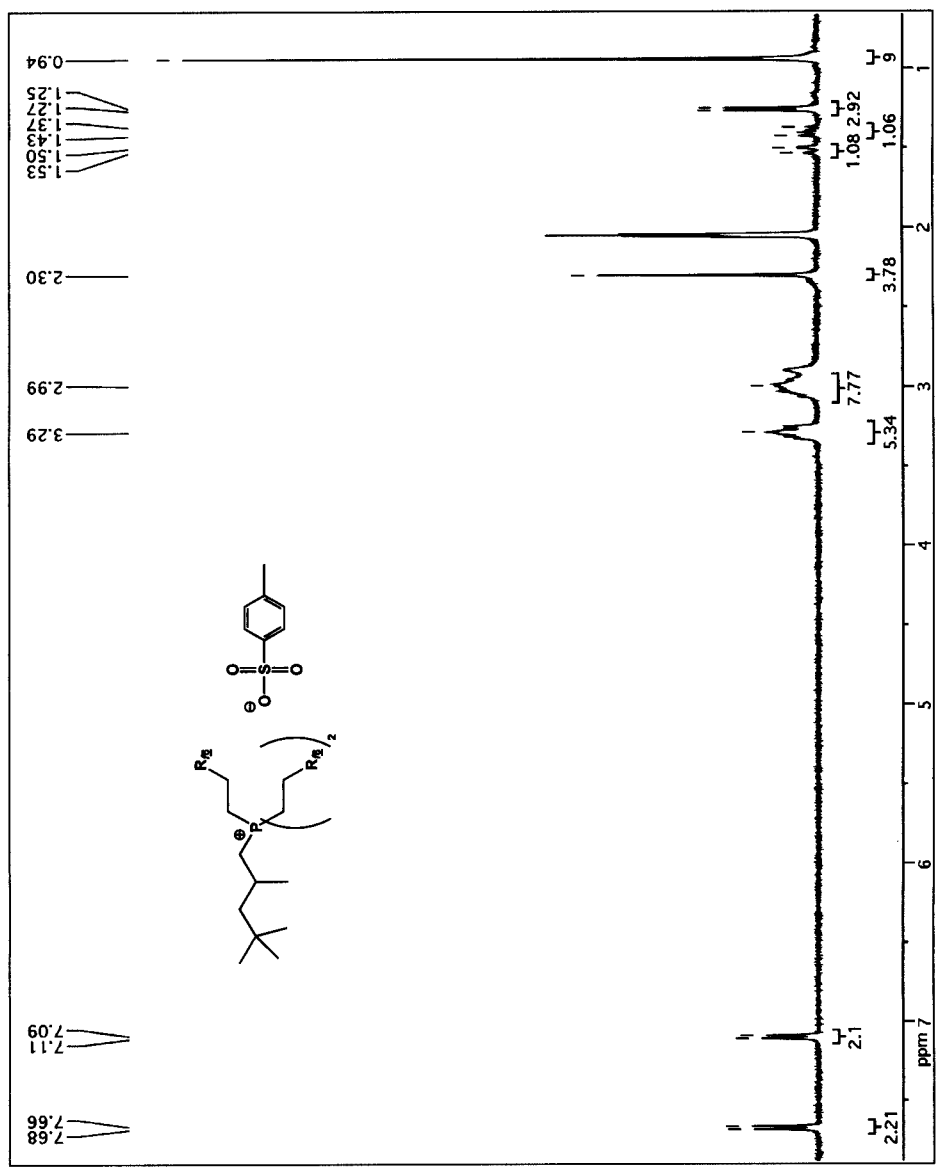
FIG. 15 shows the $^1H$ NMR spectrum of [9][OTs]

FIG. 15 shows the $^1$H NMR spectrum of [9][OTs].

[9][OTf]:

$^{19}$F{$^1$H} NMR (376.15 MHz, Acetone-d$_6$) δ (ppm); −79.5 (s, 3F).

[1][NTf$_2$]:

$^{19}$F{$^1$H} NMR (376.15 MHz, Acetone-d$_6$) δ (ppm); −80.5 (s, 6F).

Figure 16:
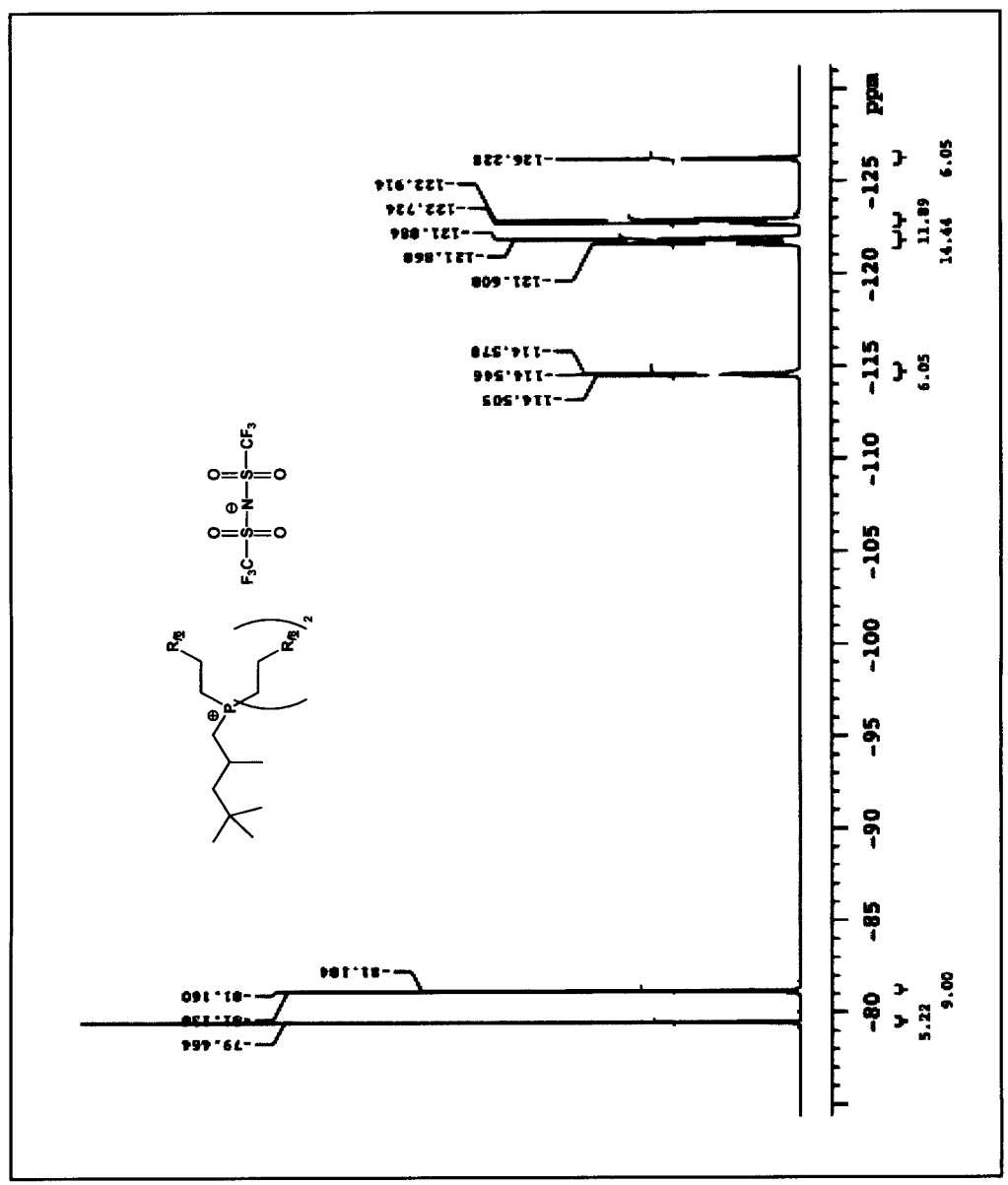
FIG. 16 shows the $^{19}F\{^1H\}$ NMR spectrum of [9][$NTf_2$]

FIG. 16 shows the $^{19}$F{$^1$H} NMR spectrum of [9][NTf$_2$].

Synthesis of Rf$_6$(CH$_2$)$_2$P(O)(O$^i$Pr)$_2$, See Reference (20).

Alterations to the referenced procedure include substituting P(OEt)$_3$ with P(O$^i$Pr)$_3$, the reaction time was reduced to from 16 h to 8 h and the product was purified by distillation instead of column chromatography (Rf$_6$(CH$_2$)$_2$P(O)(O$^i$Pr)$_2$ bp 138° C., 0.5 mmHg).

Yield; 11.29 g, 22.75 mmol, 56%; $^1$H NMR (400.09 MHz, CDCl$_3$) δ (ppm); 4.74-4.66 (sept, 2H, $^3$J$_{H-H}$=6.4 Hz), 2.40-2.24 (m, 2H, CH$_2$CF$_2$), 1.95-1.86 (m, 2H, CH$_2$P), 1.30 (d, 12H, CH(CH$_3$)$_2$); $^{31}$P{$^1$H} NMR (161.96 MHz, CDCl$_3$) δ (ppm); 26.6 (s); $^{19}$F{$^1$H} NMR (376.15 MHz, CDCl$_3$) δ (ppm); −80.7 (m, 3F), −115.2 (m, 2F), −121.8 (m, 2F), −122.8 (m, 2F), −123.3 (m, 2F), −126.1 (m, 2F).

Synthesis of Rf$_6$(CH$_2$)$_2$PH$_2$, See Reference (20).

Alterations to the referenced procedure include substituting Rf$_6$(CH$_2$)$_2$P(O)(OEt)$_2$ for Rf$_6$(CH$_2$)$_2$P(O)(O$^i$Pr)$_2$, the reaction time was reduced from 16 h to 10 min. Yield; 9.79 g, 25.76 mmol, 62%; $^1$H NMR (399.8 MHz, CDCl$_3$) δ (ppm); 3.04 (dt, 2H, $^1$J$_{H-P}$=194.8 Hz, PH$_2$), 2.36-2.22 (m, 2H, CH$_2$CF$_2$), 1.79-1.70 (m, 2H, PCH$_2$); $^{31}$P{$^1$H} NMR (161.96 MHz, CDCl$_3$) δ (ppm); −133.8 (s); $^{19}$F{$^1$H} NMR (376.15 MHz, CDCl$_3$) δ (ppm); −80.9 (t, 3F, $^3$J$_{F-F}$=10.5), −115.1 (m, 2F), −122.0 (m, 2F), −123.0 (m, 2F), −123.6 (m, 2F), −126.2 (m, 2F).

Synthesis of P[(CH$_2$)$_2$Rf$_6$]$_3$, See Reference (19).

Alterations to the referenced procedure include the use of a 20% excess of the fluorous olefin instead of a 25% excess, instead of PhPH$_2$, the primary phosphine used was Rf$_6$(CH$_2$)$_2$PH$_2$, the AIBN was substituted for VAZO 67 and the temperature was increased to 90° C. After the final addition of VAZO 67, the reaction was allowed to stir for only 3 h instead of 7 h. The diethyldimethyl-succinonitrile was removed by sublimation (−20° C. cold finger, 0.5 mmHg, 60° C. oil bath) and the oil was distilled [Rf$_6$(CH$_2$)$_2$]$_3$P bp 130° C., 0.5 mmHg).

Yield; 16.55 g, 86.06 mmol, 60%; $^1$H NMR (400.09 MHz, CDCl$_3$) δ (ppm); 2.28-2.13 (m, 2H, CH$_2$CF$_2$), 1.78-1.71 (m, 2H, PCH$_2$); $^{31}$P{$^1$H} NMR (161.96 MHz, CDCl$_3$/C$_7$H$_5$F$_3$) δ (ppm); −24.6 (s); $^{19}$F{$^1$H} NMR (376.15 MHz, CDCl$_3$) δ (ppm); −80.9 (m, 3F), −114.9 (m, 2F), −122.0 (m, 2F), −122.9 (m, 2F), −123.4 (m, 2F), −126.2 (m, 2F).

Synthesis of CH$_3$(CO)S(CH$_2$)$_{12}$Br, See Reference (21).

Alterations to the referenced procedure include the substitution of 2-(12-Bromododecyl)-1,4-dimethoxybenzene for 1,12-dibromododecane, the product was extracted in CH$_2$Cl$_2$ and H$_2$O instead of toluene and H$_2$O and the product was purified by column chromatography (10:1 hexane:ethyl acetate). Yield; 6.30 g, 19.43 mmol, 79%; $^1$H NMR (400.09 MHz, CDCl$_3$) δ (ppm); 3.41 (t, 2H, $^3$J$_{H-H}$=6.8 Hz, BrCH$_2$), 2.86 (t, 2H, $^3$J$_{H-H}$=7.4 Hz, SCH$_2$), 2.32 (s, 3H, CH$_3$CO), 1.85 (quintet, 2H, $^3$J$_{H-H}$=7.2 Hz, BrCH$_2$CH$_2$), 1.56 (quintet, 2H, $^3$J$_{H-H}$=6.8 Hz, SCH$_2$CH$_2$), 1.46-1.26 (m, 16H, CH$_2$).

Synthesis of HS(CH$_2$)$_{12}$Br, See Reference (21).

Alterations to the referenced procedure include the substitution of S-12-(2,5-dihydroxyphenyl)dodecyl ethanethioate with CH$_3$(CO)S(CH$_2$)$_{12}$Br and K$_2$CO$_3$ for concentrated HCl, the reaction time was reduced from 12 h to 5 h and the product was purified by sublimation (−20° C. cold finger, 0.5 mmHg, 70° C. oil bath). Yield; 3.47 g, 12.32 mmol, 89%; $^1$H NMR (400.09 MHz, CDCl$_3$) δ (ppm); 3.40 (t, 2H, $^3$J$_{H-H}$=7.2 Hz, BrCH$_2$), 2.51 (dt, 2H, $^3$J$_{H-H}$=7.2 Hz, HSCH$_2$), 1.84 (quintet, 2H, $^3$J$_{H-H}$=7.2 Hz, BrCH$_2$CH$_2$), 1.60 (quintet, 2H, $^3$J$_{H-H}$=7.2 Hz, HSCH$_2$CH$_2$), 1.44-1.26 (m, 17H, CH$_2$ and SH t, $^3$J$_{H-H}$=7.6 Hz). 13C NMR (100.60 MHz, CDCl$_3$) δ (ppm); 45.14, 34.01, 32.80, 32.61, 29.45, 29.03, 28.85, 28.72, 28.33, 28.14, 26.84, 24.62.

Synthesis of [10][Br].

A pressure tube was charged with 1-bromo-12-mercaptododecane (2.62 g, 9.33 mmol) in DMF (15 mL) and P[(CH$_2$)$_2$Rf$_6$]$_3$ (5.00 g, 4.66 mmol) in trifluorotoluene (15 mL) under nitrogen and heated at 130° C. for 24 h. The solvent was removed in vacuo at 100° C. and the impurities were removed by sublimation (110° C.; −20° C. cold finger) and the liquid was further purified by dissolving in a minimal amount of trifluorotoluene and extracted with 1:1 n-pentane:toluene mixture. Excess solvent was decanted and the residual volatiles were removed in vacuo resulting in a clear dark orange viscous liquid (3.71 g, 2.74 mmol, 59%). $^1$H NMR (599.69 MHz, Acetone-d$_6$) δ (ppm); 3.45-3.39 (m, 6H, CH$_2$CF$_2$), 3.25-3.20 (m, 2H, PCH$_2$CH$_2$CH$_2$), 3.07-2.99 (m, 6H, PCH$_2$CH$_2$CF$_2$), 2.50 (dt, 2H, $^3$J$_{H-H}$=7.8 Hz, HSCH$_2$), 1.87-1.83 (m, 2H, PCH$_2$CH$_2$CH$_2$), 1.66 (t, 1H, $^3$J$_{H-H}$=7.8 Hz, HS), 1.59-1.53 (m, 4H, CH$_2$), 1.44-1.37 (m, 4H, CH$_2$), 1.32-1.29 (m, 10H, CH$_2$). $^{19}$F{$^1$H} NMR (376.15 MHz, Acetone-d$_6$) δ (ppm); −81.2 (s, 9F), −114.4 (m, 6F), −121.9 (m, 6F), −122.8 (m, 12F), −126.3 (m, 6F); $^{31}$P{$^1$H} NMR (161.83 MHz, Acetone-d$_6$) δ (ppm); 40.1 (s); MS (ESI); m/z$^{+/−}$ (%): 1271.1 (100) [M$^+$-Br], 2623.0 (15) [M$_2$Br$^+$], 3974.0 (1) [M$_3$Br$_2^+$], 1430.6 (100) [MBr$_2^-$], 2782.3 (12) [M$_2$Br$_3^-$], 4133.9 (2) [M$_3$Br$_4^-$]; FT-IR (cm$^{-1}$(ranked intensity)); 456(20), 530(6), 566(13), 605(19), 707(7), 736(11), 780(15), 810(12), 846(17), 913(18), 951(14), 1020(16), 1071(8), 1259(3), 1317(5), 1365(4), 1438(9), 1717(21), 2462(22), 2858(2), 2929(1).

Figure 17:
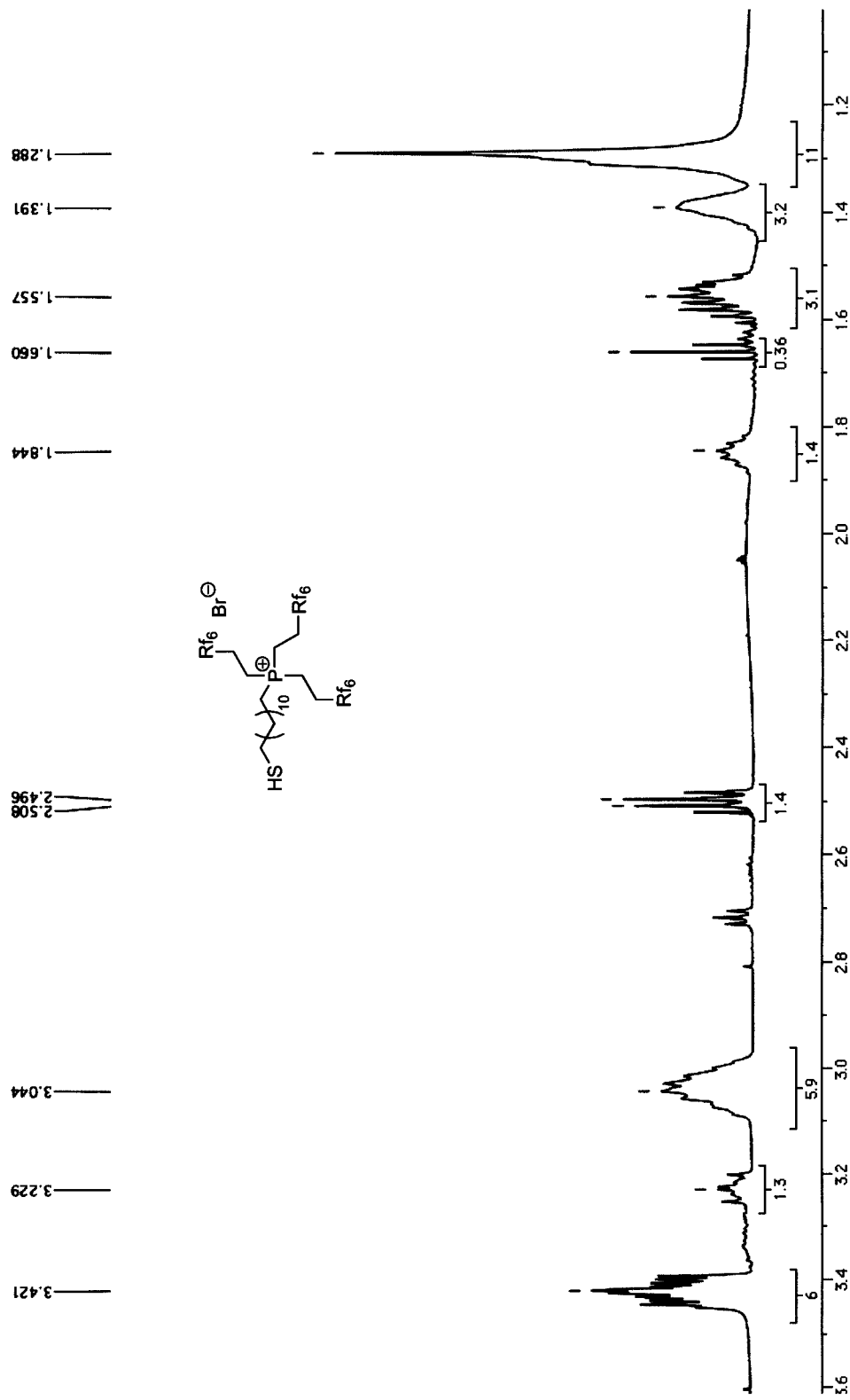
FIG. 17 shows the $^1H$ NMR spectrum of [10][Br]
Figure 18:
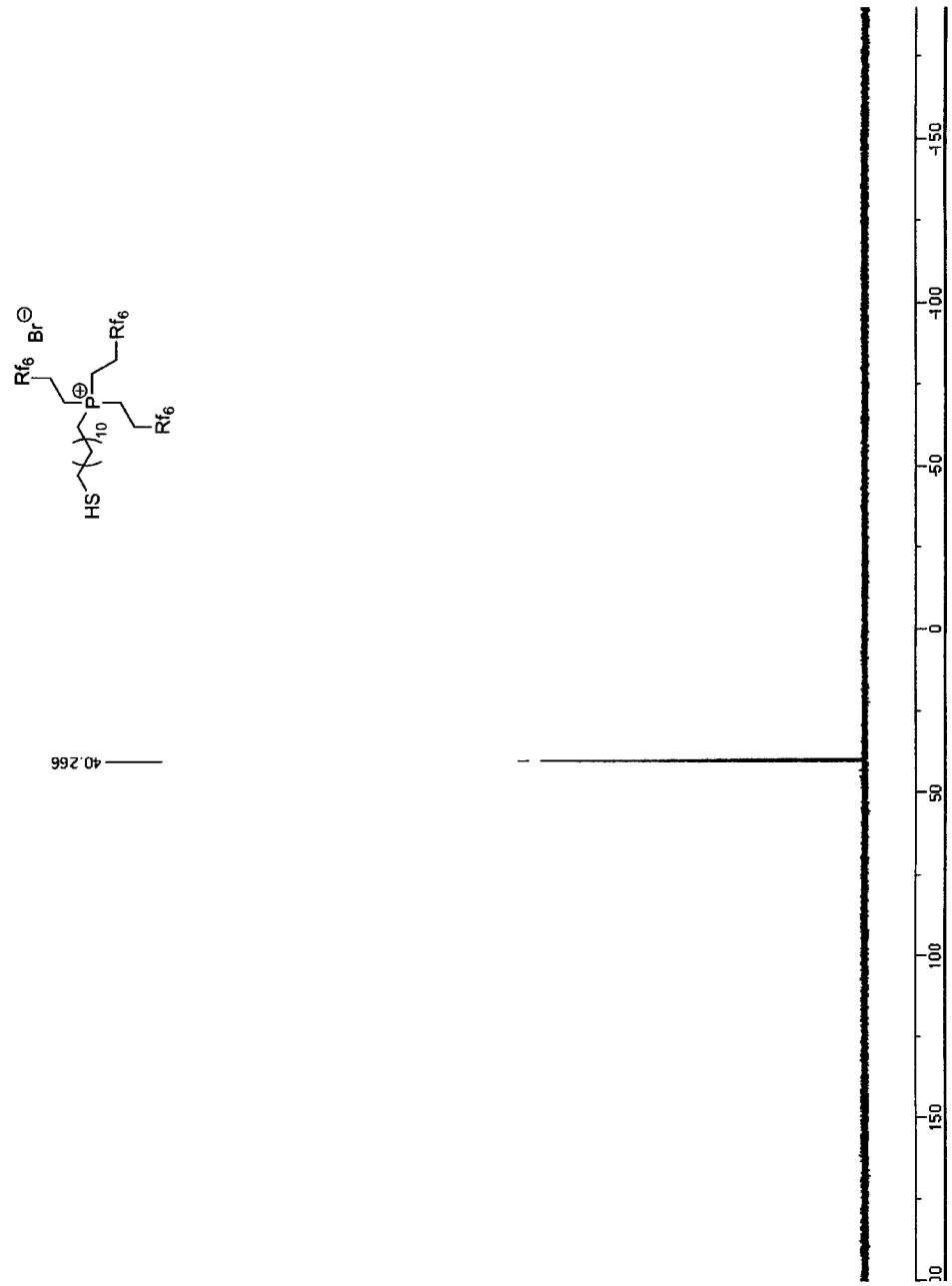
FIG. 18 shows the $^{31}P\{^1H\}$ NMR Spectrum of [10][Br]
Figure 19:
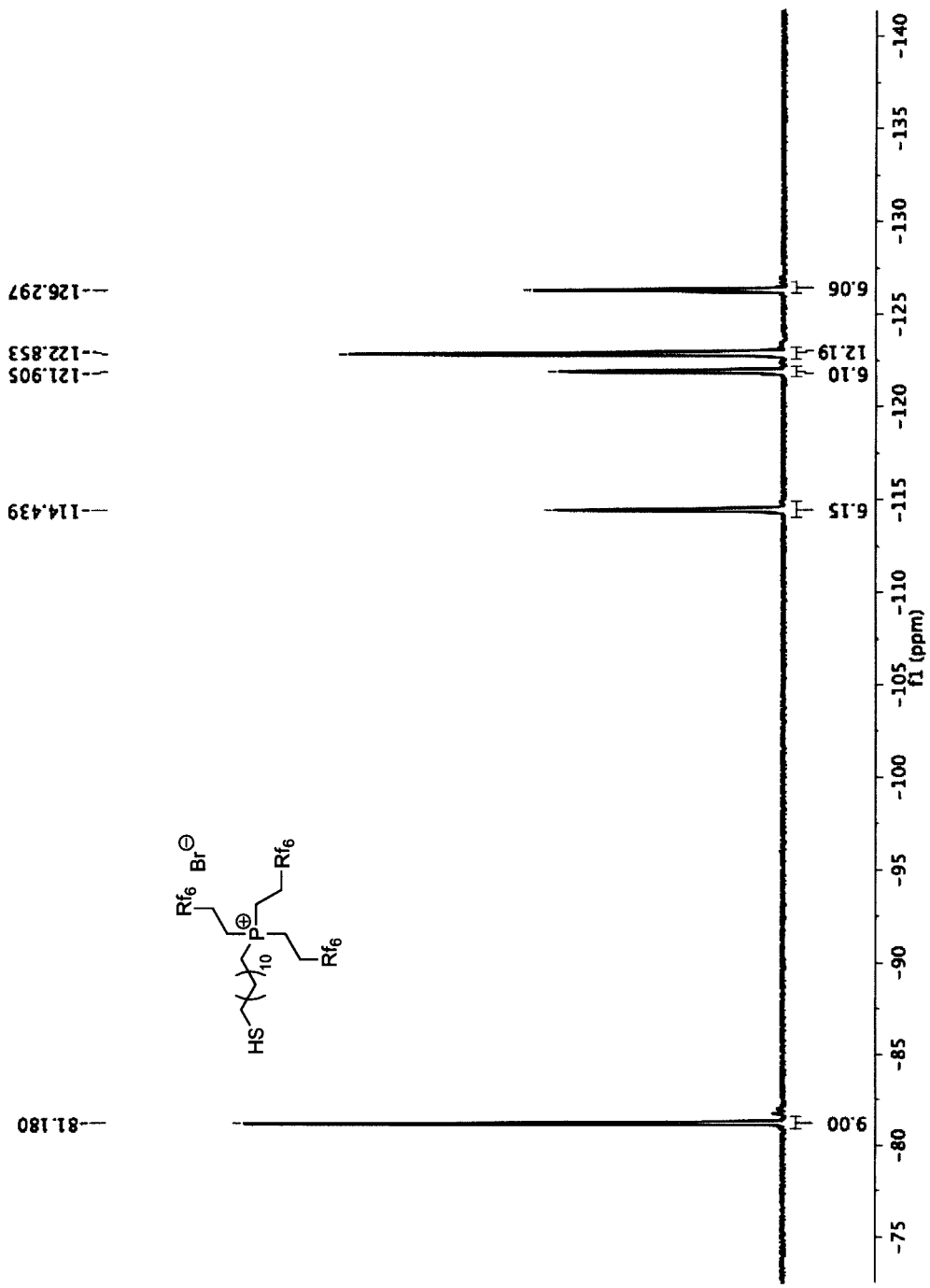
FIG. 19 shows the $^{19}F\{^1H\}$ NMR Spectrum of [10][Br].

FIG. 17 shows the $^1$H NMR spectrum of [10][Br] and FIG. 18 shows the $^{31}$P{$^1$H} NMR Spectrum of [10][Br]. FIG. 19 shows the $^{19}$F{$^1$H}NMR Spectrum of [10][Br].

Synthesis of [10][NTf$_2$].

Lithium bistriflimide (0.65 g, 2.26 mmol) in acetone (5 mL) was added dropwise to [10][Br] (1.53 g, 1.13 mmol) in acetone (25 mL) under nitrogen and was stirred for 44 h. The solvent was removed in vacuo and the salt was re-dissolved in trifluorotoluene (25 mL), filtered and then transferred to a Schlenk tube. The solution was extracted with degassed H$_2$O (3×60 mL) and then dried with MgSO$_4$, filtered and the solvent was removed in vacuo. The impurities were removed by sublimation (110° C.; −20° C. cold finger) and the liquid was further purified by dissolving in a minimal amount of trifluorotoluene and extracted with Et$_2$O. The residual solvent and water was removed in vacuo at 90° C. for 36 h yielding a brown liquid (0.82 g, 0.53 mmol, 47%). $^1$H NMR (599.69 MHz, Acetone-d$_6$) δ (ppm); 3.27-3.23 (m, 6H, CH$_2$CF$_2$), 3.07-2.93 (m, 8H, PCH$_2$CH$_2$CH$_2$, PCH$_2$CH$_2$CF$_2$), 2.50 (dt, 2H, $^3$J$_{H-H}$=7.8 Hz, HSCH$_2$), 1.96-1.89 (m, 2H, PCH$_2$CH$_2$CH$_2$), 1.63 (t, 1H, $^3$J$_{H-H}$=7.8 Hz, HS), 1.60-1.54 (m, 4H, CH$_2$), 1.41-1.36 (m, 4H, CH$_2$), 1.32-1.28 (m, 10H, CH$_2$). $^{19}$F{$^1$H} NMR (376.15 MHz, Acetone-d$_6$) δ (ppm); −79.5 (s, 6F), −81.2 (s, 9F), −114.7 (m, 6F), −121.9 (m, 6F), −123.0 (m, 12F), −126.3 (m, 6F); $^{31}$P{$^1$H} NMR (161.83 MHz, Acetone-d$_6$) δ (ppm); 41.3 (s); MS (ESI); m/z$^{+/−}$ (%): 1273.9 (100) [M$^+$-(NTf$_2$)], 2821.6 (10) [M$_2$(NTf$_2$)$^+$], 1833.0 (65) [M(NTf$_2$)$_2^-$]. FT-IR (cm$^{-1}$(ranked intensity)); 513(12), 531(16), 571(9), 618(5), 652(10), 708(7), 741(8), 790(14), 810(13), 847(17), 913(19), 952(15), 1100(6), 1244(2), 1348 (3), 1441(18), 2386(21), 2859(11), 2981(1). Anal. Calcd. (Found) C, 29.39 (30.14); H, 2.39 (2.10).

Results and Discussion

Figure 2:
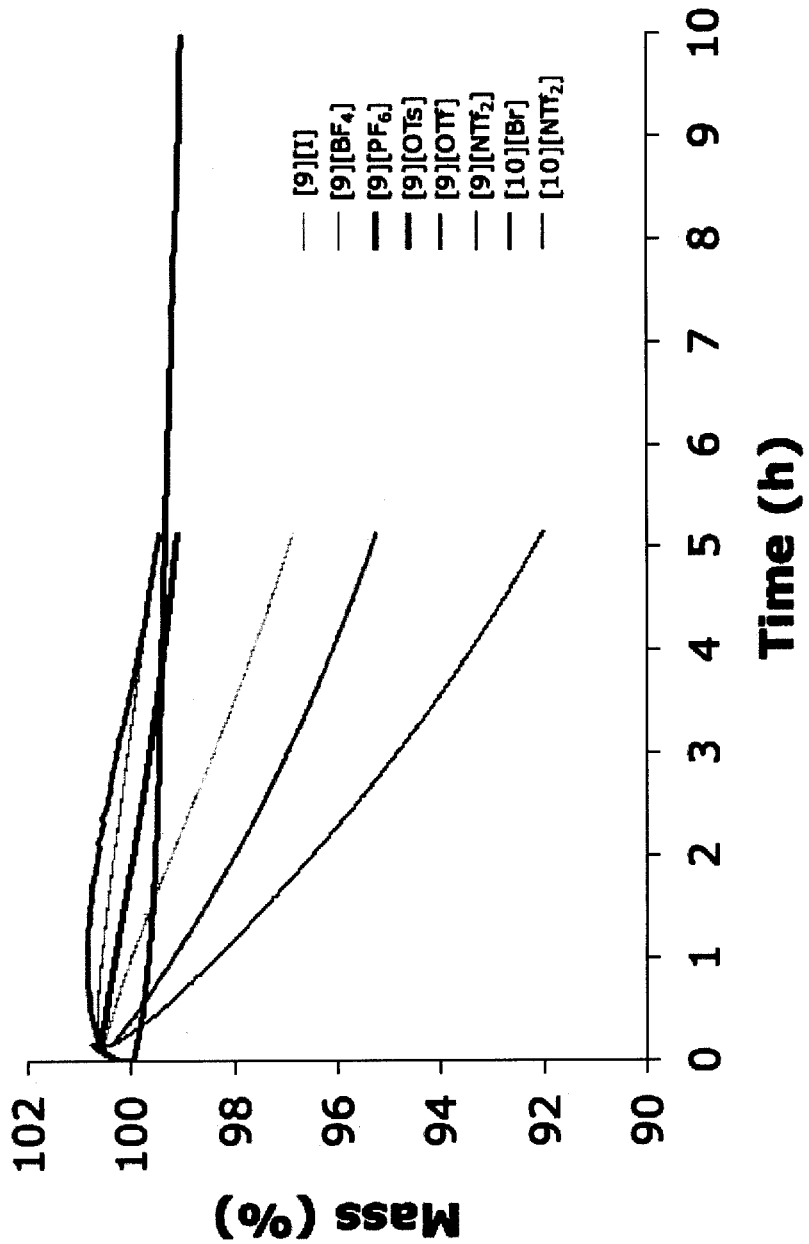
FIG. 2 shows the isothermal thermal gravimetric analysis (TGA) plots for several ionic liquids from the two classes [9] and [10] for which the DSC and TGA curves are given in FIGS. 1a) and b)
Figure 4:
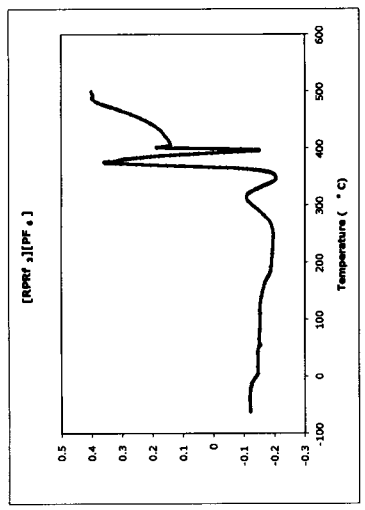
FIG. 4 shows the thermal stability of [9][$NTf_2$] determined by DSC.
Figure 5:
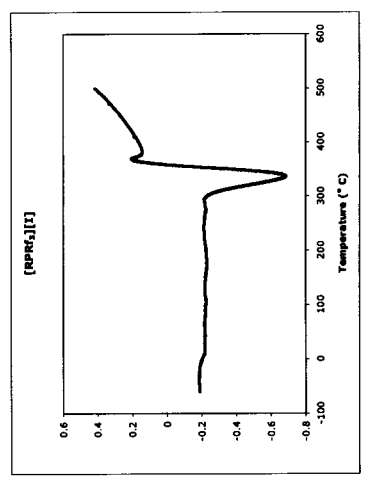
FIG. 5 shows the thermal stability of [9][$PF_6$] determined by DSC.
Figure 3:
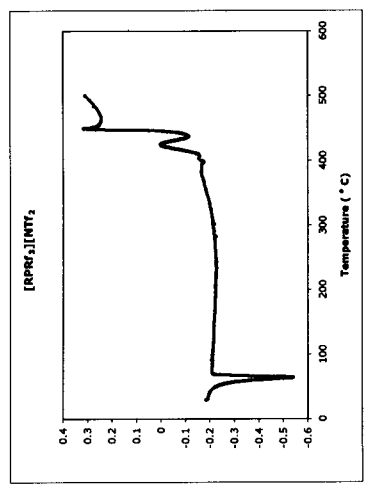
FIG. 3 shows the thermal stability of [9][OTf] determined by differential scanning calorimetry (DSC)
Figure 7:
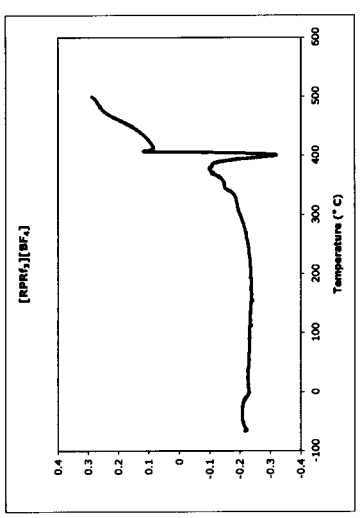
FIG. 7 shows the thermal stability of [9][$BF_4$] determined by DSC.
Figure 6:
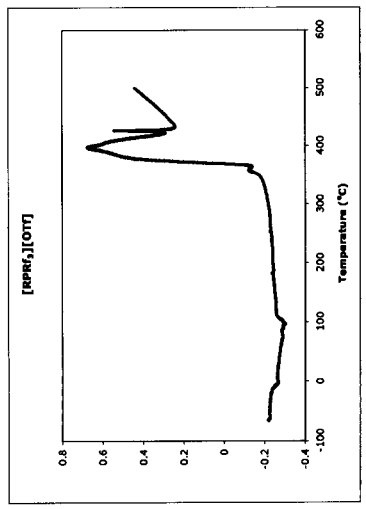
FIG. 6 shows the thermal stability of [9][OTs] determined by DSC.
Figure 8:
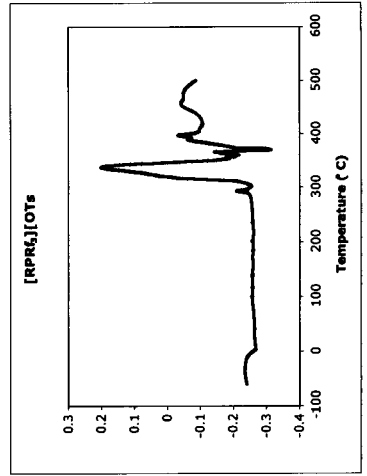
FIG. 8 shows the thermal stability of [9][I] determined by DSC.

In all cases the ionic liquids have glass transition temperatures ($T_g$) determined by DSC, that range from −5° C. to −35° C. (Table 1, FIG. 1a)) and they are all tacky liquids at ambient temperatures with the exception of [9][NTf$_2$], which is a waxy solid. There are no crystallization or melting transitions observed for the glassy highly fluorinated phosphonium ionic liquids indicating that the materials are completely amorphorous. Upon warming to between 60° C. and 80° C., all of the compounds become free flowing, stirable liquids, where the specific temperature is dependent on the cation/anion pairing. The thermal stability of the phosphonium ionic liquids was determined using TGA under both dynamic and isothermal heating environments. Heat ramp analysis of the ionic liquids determined decomposition temperatures ($T_d$) in the range of 311° C. to 407° C. (Table 1, FIG. 1b)). A minimal mass loss (c.a. 2% to 4%) was observed for derivatives of (9) when they were subjected to constant heating (120° C.) for extended periods of time (>5 h) while the thiol derivatives displayed higher thermal stability with 1% mass loss at 180° C. over 10 h, thus indicating that the materials would be sufficiently stable for use under a wide variety of conditions, (FIG. 2). Further DSC studies where (9) was cooled at −70° C. for 15 minutes and then heated to 500° C. at 10° C./min concluded no phase transition or exotherm indicative of a decomposition with zero mass loss was observed below the decomposition points noted (FIGS. 3-8). The concentration of water remaining in the PIL, determined by Karl Fischer titration was minimal, 0-1 mM, see Table 1.

Figure 9:
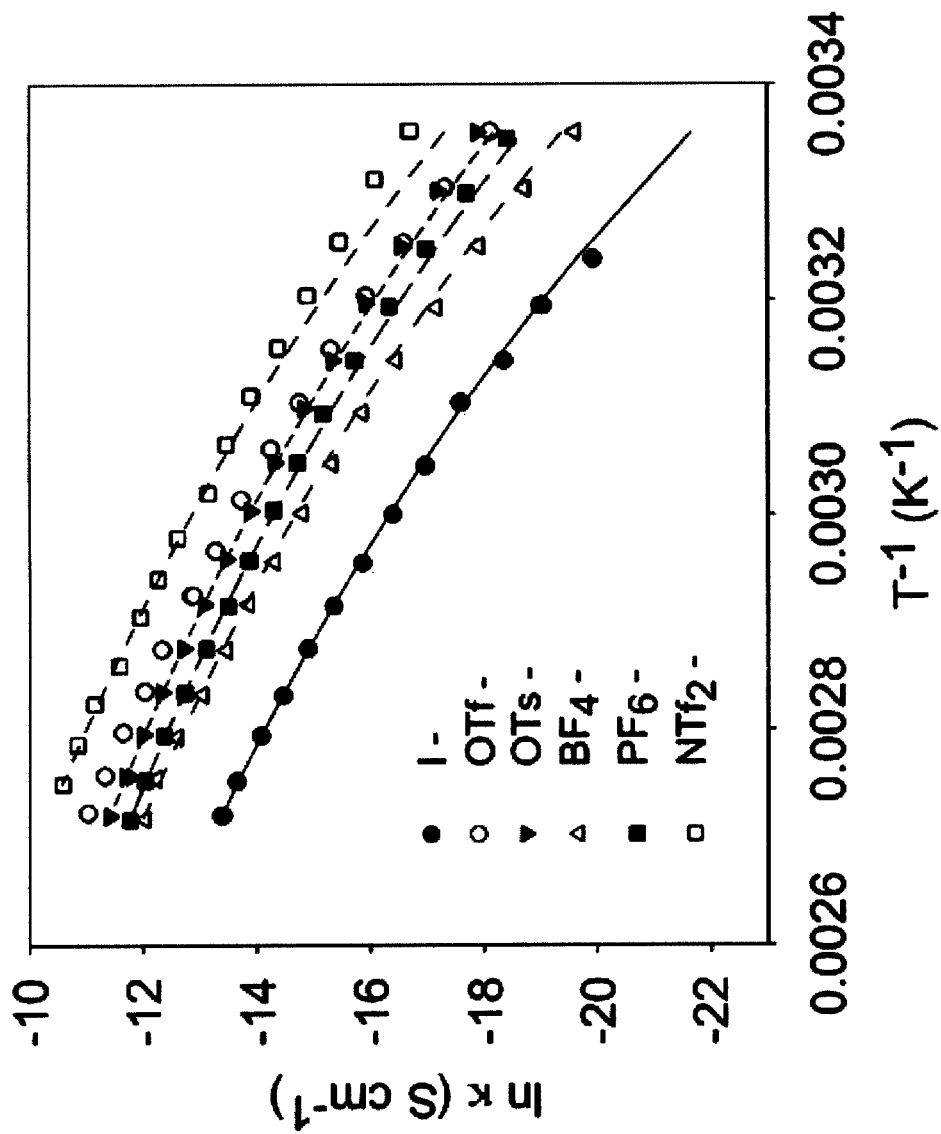
FIG. 9 shows the Arrhenius plots for ionic conductivity of [9][A] in which the lines are plots of the best fit Volgel-Tammann-Fulcher (VTF) equations.

The conductivity of phosphonium ionic liquids is almost completely unexplored; no data exists for these materials with highly fluorinated substituents. Conductivity measurements for derivatives of [9][A], obtained as a function of temperature, revealed a negative deviation from linear Arrhenius behaviour consistent with glass-forming liquids (FIG. 9). The data for [9][A] follow the empirical Vogel-Tammann-Fulcher (VTF)$^a$ equation, where A and B are constants, and $T_o$ is the temperature at which the conductivity goes to zero, see reference (1). The constants A and B that gave the best fit to the equation are listed in Table 3 and the conductivity values observed at 25° C. are reported in Table 2 entitled VTF Equation Parameters for Ionic Conductivity Data.

Compared to the 25° C. conductivity data reported for other non-phosphonium cation-based ionic liquids that are typically in the range of 1-10 mS·cm$^{-1}$, compounds [9][A] exhibit much smaller conductivity, ranging from 0.0004 to 0.06 μS·cm$^{-1}$. These values are similar to those reported for phosphonium halide salts, see reference (1) and (22), and are lower by approximately a factor of 10, than phosphonium sulfonylamide systems with nonfluorinated substituents, see reference (23). Although the room temperature conductivity of the PILs is small, it has a large Arrhenius temperature dependence, where the constant B in the VTF equation is on the range of 1600-1900 K$^{-1}$, higher than the 600-1000 K$^{-1}$ reported for imidazolium- and pyridinium-based ILs, see reference (24). As a result, the ionic conductivity of the PILs rises rapidly with temperature and varies with the anion, decreasing in the order NTf$_2^-$>OTs$^-$, OTf$^-$, PF$_6^-$, BF$_4^-$>I$^-$.

Sensitivity to UV light is a problem amongst other hydrophobic coatings and leads to decomposition of the material. Given the potential applications of such coatings, which typically would involve interactions with the environment, including UV light, a sufficient resiliency to UV exposure is required. Compound [9][I] was continuously exposed to UV irradiation for 12 hours and subsequent analysis of the material by multinuclear NMR spectroscopy, revealed no detectable decomposition.

Highly fluorinated organic molecules often display temperature dependent miscibilities with common hydrocarbon solvents. All derivatives of (9) form biphasic systems with common laboratory solvents of ranging polarity at room temperature. However, at elevated temperatures, a monophasic system is formed with THF and CH$_2$Cl$_2$ and upon cooling to 0° C., the biphasic mixture is reformed. In the PIL/THF mixture some contamination of the THF layer with the PIL was evident even after cooling to −30° C. (2-6%) see Table 3. This is comparable to the contamination of fluorocarbon solvents used in similar applications, see reference (25), indicating that the fluorous PILs are well suited for fluorous biphasic applications.

Figure 10:
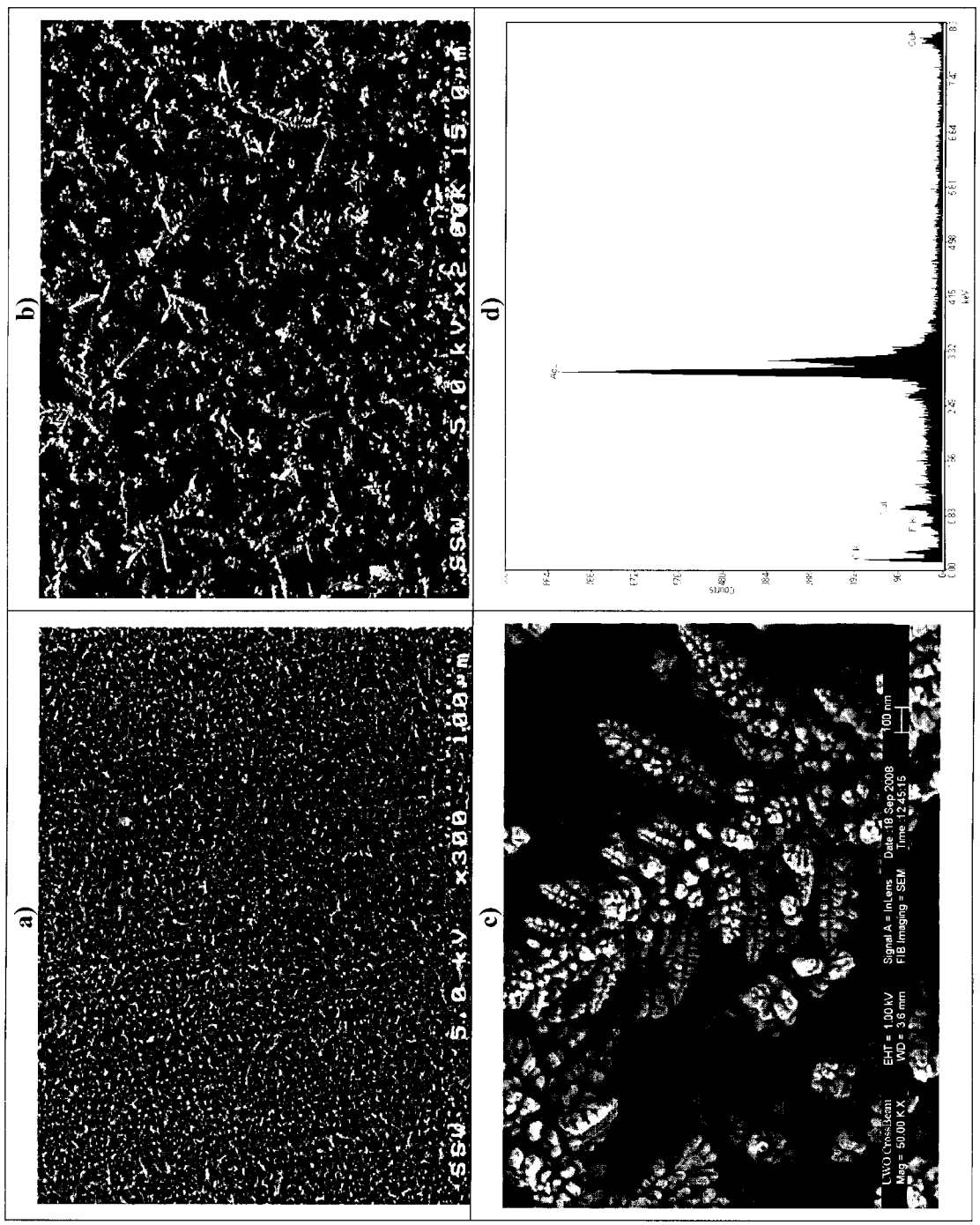
FIG. 10a), b) and c) show SEM images of the silver plated copper substrate at different magnifications d) shows EDX analysis of silver plated copper substrate with [9][$NTf_2$] coating.

Based on the solvent miscibility experiments with water and the high fluorine loading, the PILs showed obvious evidence of hydrophobic character. Using the straightforward procedure reported by Larmour et al., which involves the electroless galvanic deposition of Ag on a copper surface, a substrate with sufficient geometrical roughness on the nano- and micron scale was achieved, see reference (26). The hydrophobic coating was prepared by immersing the Ag coated Cu plate in a highly dilute solution of the PIL (8.15 mM) either by dip coating (series (9)) or submerging the substrate in the solution for 15 minutes (series al)). The surface was characterized by SEM and EDX analysis, which confirmed a uniform silver covering with notable crystallite microstructures, and the necessary roughened texture, see FIG. 10.

Figure 11:
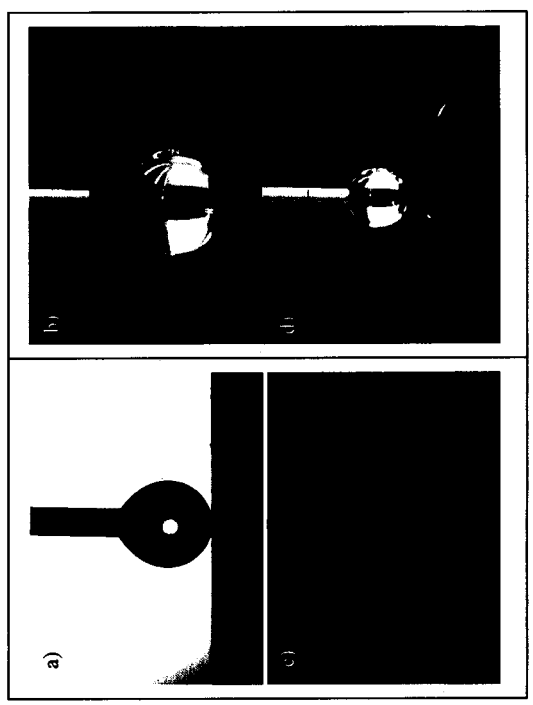
FIG. 11 shows water contact angle measurements; a) [9][$NTf_2$] coating, detaching droplet (θ=168°); b) [10][Br] coating, static droplet (θ=165°); c) [9][$BF_4$] coating, after acetone wash (θ=129°); d) substrate without a PIL coating (θ=30°)

The hydrophobicity of the prepared surfaces was evaluated by static water contact angle measurements and all of the surfaces were determined to be superhydrophobic (FIG. 11, Table 1). In some cases a static contact angle could not be measured as the superhydrophobic nature of the surfaces precluded our ability to deposit a resting drop. Therefore, alternative methods were applied using the technique described by Gao et al, see reference (27).

The nature of the counteranion appears to effect the degree of superhydrophobicity; the highly fluorinated anions (NTf$_2^-$, PF$_6^-$, BF$_4^-$) do indeed produce materials with a greater contact angle. However, all derivatives reduce water wettability in comparison to the Ag coated Cu plates without the PIL coating (θ≈30°). Re-examination of the PIL coated surfaces by SEM after the water contact angles were measured, revealed virtually no surface disturbance. To evaluate the hypothesis of enhancing the retention of the surface coating with the thiol highly fluorinated phosphonium ionic liquid derivatives (10) in comparison to the physisorbed (9), the coated substrates were immersed for 10 minutes in acetone, which readily solubilizes the highly fluorinated phosphonium ionic liquid, and water contact angle measurements were again obtained. Given the contact angle remains consistent for (10) and decreases substantially for (9)(e.g. [9][BF4] θ=129°), it provides strong evidence for a significant increase in resiliency and the presence of an Ag—S bond in (10).

While the synthetic routes have been presented above for the synthesis of series 9 and 10, it will be appreciated that the method of synthesis will vary depending on the particular molecule (11) that is desired for the application at hand. For example, the specific molecule from series (10) synthesized above used had Z being a thiol functional group (HS) to give chemisorption to the silver coated copper substrate. If any of the other disclosed functional groups Z disclosed herein, a different synthesis route would be needed which will be solely dependent on the functional group. The particular synthesis routes will be well known to those skilled in the art.

A new class of phosphonium ionic liquids, which are highly fluorinated, thermally stable and viscous liquids at room temperature were prepared and comprehensively characterized. Deposited films of the highly fluorinated phosphonium ionic liquid materials on Ag coated Cu substrates were capable of producing water contact angles greater than 160° indicating that highly fluorinated phosphonium ionic liquids are uniquely suited for superhydrophobic coatings. Introducing a thiol functionality to the cation allows for the generation of a film with increased durability, emphasizing that ionic liquids are not only new alternative solvents, but also viable functional materials, offering a new paradigm for their potential applications.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

TABLE 1

Characteristics of the Highly Fluorinated Ionic Liquids Series (9) and (10)

| Entry | PIL | $T_g$ (° C.) | $T_d$ (° C.) | WCA (°) | Avg H$_2$O Content |
|---|---|---|---|---|---|
| 1 | [9][I] | −5 | 316 | 156, 159$^c$ | 0 |
| 2 | [9][BF$_4$] | −14 | 311 | 161, 166$^c$ | 0.556 |
| 3 | [9][PF$_6$] | −14 | 354 | 159, 160$^c$ | 0 |
| 4 | [9][OTf] | −14 | 347 | 155 | 0.779 |
| 5 | [9][OTs] | −11 | 396 | 153 | 1.019 |
| 6 | [9][NTf$_2$] | −25 60$^a$ | 407 | 168$^c$ | 0 |
| 7 | [10][Br] | −15 | 335 | 163 | — |
| 8 | [10][NTf$_2$] | −35 | 389 | 168 | — |

PIL = Phosphonium Ionic Liquid,
$^a$Melting point,
$^b$Onset of decomposition,
$^c$Detaching contact angle.

TABLE 2

Conductivity data for compound 9.

| [A] | κ (μS · cm$^{-1}$) 25° C. | A (S cm$^{-1}$) | B (K) | $T_o$ (K) | $R^2$ |
|---|---|---|---|---|---|
| I | 0.0004$^b$ | 2.2 | 1826 | 205 | 0.99 |
| BF$_4$ | 0.003 | 4.3 | 1764 | 200 | 0.99 |
| PF$_6$ | 0.010 | 2.8 | 1654 | 200 | 0.99 |
| OTs | 0.017 | 3.5 | 1633 | 199 | 0.99 |
| OTf | 0.013 | 13.9 | 1849 | 194 | 0.99 |
| NTf$_2$ | 0.056 | 13.2 | 1670 | 200 | 0.99 |

$^a$κ = A(T)$^{0.5}$ [exp (− B/(T − $T_o$))],
$^b$Extrapolated to 25° C. with the VTF equation using the best fit parameters.

TABLE 3

Temperature Dependent Solvent Miscibility Study Results for Series (9)

| | n-hex. | | Tol. | | DCM | | THF | | TFT | | Contamination of THF in PIL (%) | |
|---|---|---|---|---|---|---|---|---|---|---|---|---|
| [A] | 22° C. | 90° C. | 22° C. | 90° C. | 22° C. | 90° C. | 22° C. | 90° C. | 22° C. | 90° C. | 22° C. | −30° C. |
| [OTf] | I | I | I | I | I | I | I | M | M | M | 14 | 4 |
| [NTf$_2$] | I | I | I | I | I | SM | I | M | M | M | 10 | 4 |
| [BF$_4$] | I | I | I | I | I | I | I | M | M | M | 5 | 5 |
| [PF$_6$] | I | I | I | I | I | SM | I | M | M | M | 10 | 4 |
| [OTs] | I | I | I | I | I | SM | I | M | M | M | 14 | 2 |
| [I] | I | I | I | I | I | SM | SM | M | M | M | 10 | 6 |

REFERENCES (1) Wasserscheid, P.; Welton, T. Ionic Liquids in Synthesis; Wiley-VCH: Germany, 2003.
(2) Tao, G.-h.; He, L.; Sun, N.; Kou, Y. *Chem. Commun.* 2005, 3562-3564.
(3) Tao, G.-h.; He, L.; Liu, W.-s.; Xu, L.; Xiong, W.; Wang, T.; Kou, Y. *Green Chem.* 2006, 8, 639-646.
(4) Fukumoto, K.; Hiroyuki, O. *Chem. Commun.* 2006, 3081-3083.
(5) Fukumoto, K.; Yoshizawa, M.; Ohno, H. *J. Am. Chem. Soc.* 2005, 127, 2398-2399. Fukumoto, K.; Ohno, H. *Angew. Chem. Int. Ed.* 2007, 46, 1852-1855.
(7) Audic, N.; Clavier, H.; Mauduit, M.; Guillemin, J.-C. *J. Am. Chem. Soc.* 2003, 125, 9248-9249.
(8) van den Broeke, J.; Winter, F.; Deelman, B.-J.; van Koten, G. *Org. Lett.* 2002, 4, 3851-3854.
(9) a) Merrigan, T. L.; Bates, E. D.; Dorman, S. C.; Davis, J. H., Jr. *Chem. Commun.* 2000, 2051-2052. b) Xue, H.; Shreeve, J. M. Eur. J. *Inorg. Chem.* 2005, 2573-2580.
(10) a) Emnet, C.; Weber, K. M.; Vidal, J. A.; Consorti, C. S.; Stuart, A. M.; Gladysz, J. A. *Adv. Synth. Catal.* 2006, 348, 1625-1634. b) Consorti, C. S.; Jurisch, M.; Gladysz, J. A. *Org. Lett.* 2007, 9, 2309-2312.
(11) Borra, E. F.; Seddiki, O.; Angel, R.; Eisenstein, D.; Hickson, P.; Seddon, K. R.; Worden, S. P. *Nature.* 2007, 447, 979-981.
(12) Rutten, F. J. M.; Tadesse, H.; Licence, P. *Angew. Chem.* 2007, 119, 4241-4243.
(13) Liu, X.; Zhou, F.; Liang, Y.; Liu, W. *Tribology Letters.* 2006, 23, 191-196.
(14) Liu, Y.; Shi, L.; Wang, M.; Li, Z.; Liu, H.; Li, J. *Green. Chem.* 2005, 7, 655-658.
(15) Horváth, I. T. *Acc. Chem. Res.* 1998, 31, 641-650.
(16) US 2007/0026460 A1.
(17) Feng, X.; Liang, L. *Adv. Mater.* 2006, 18, 3063.
(18) Prevedouros, K.; Cousins, I. T.; Buck, R. C.; Korzeniowski, S. H. *Environ. Sci. Technol.* 2006, 40, 32-44.

(19) Vlád, G.; Richter, F. U.; Horváth, I. T. *Tetrahedron Lett.* 2005, 46, 8605-8608.
(20) Emnet, C.; Gladysz, J. A. *Synthesis* 2005, 1012-1018.
(21) Shamsipur, M.; Kazemi, S. H.; Alizadeh, A.; Mousavi, M. F.; Workentin, M. S. *J. Electroanal. Chem.* 2007, 610, 218-226.
(22) Ramirez, R. E.; Torres-Gonzalez, L. C.; Sanchez, E. M. *J. Electrochem. Soc.* 2007, 154, B229.
(23) Wooster, T. J.; Johanson, K. M.; Fraser, K. J.; MacFarlane, D. R.; Scott, J. L. *Green Chem.* 2006, 8, 691.
(24) Noda, A.; Hayamizu, K.; Watanabe, M. *J. Phys. Chem. B* 2001, 105, 4603.
(25) Barthel-Rosa, L. P.; Gladysz, J. A. *Coord. Chem. Rev.* 1999, 190-192, 587-605.
(26) Larmour, I. A.; Bell, S. E. J.; Saunders, G. C. *Angew. Chem. Int. Ed.* 2007, 46, 1710-1712.
(27) Gao, L.; McCarthy, T. J. *J. Am. Chem. Soc.* 2006, 128, 9052-9053.

Therefore what is claimed is:

1. A phosphonium ionic liquid (11),

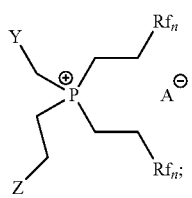

$Rfn = (CF_2)_{n-1}CF_3$ wherein Y is selected from the group consisting of $Rf_n=(CF_2)_{n-1}CF_3$; n=1-25, —$NO_2$, —CN, —OH, —$CF_3$, —COR, —SH, —OMe, —SMe, —SPh, —SSR, —COOH, —COOR, —$NH_2$, —NHR, —$NR_2$, —Si$(OC_2H_5)_3$, $C_2$-$C_{20}$ alkenyl, $C_1$-$C_{20}$ alkoxy, $C_2$-$C_{20}$ alkynyl, $C_3$-$C_8$ cycloalkyl, $C_1$-$C_{20}$ aminoalkyl, $C_1$-$C_6$ hydroxyalkyl, $C_1$-$C_{12}$ heteroaryl, $C_1$-$C_{12}$ heterocycle, fluoralkyl, and $C_2$-$C_{20}$ alkyl wherein a terminal carbon of the $C_2$-$C_{20}$ alkyl chain is substituted with a crosslinkable group selected from the group consisting of acrylate, methacrylate, norbornadienyl, styrenyl, alkenyl, alkynyl, maleimidyl and anthracenyl, a polymerizable group selected from the group consisting of acrylate, methacrylate, norbornadienyl, styrenyl, alkenyl, alkynyl, maleimidyl, [1]metalloarenophanyl and [2]metalloarenophanyl, or a substituent selected from the group consisting of —$NO_2$, —CN, —OH, —$CF_3$, —COR, —SH, —OMe, —SMe, —SPh, —SSR, —COOH, —COOR, —$NH_2$, —NHR, —$NR_2$, —Si$(OC_2H_5)_3$, $C_2$-$C_{20}$ alkenyl, $C_1$-$C_{20}$ alkoxy, $C_2$-$C_{20}$ alkynyl, $C_6$-$C_{20}$ alkyl, $C_6$-$C_{12}$ aryl, $C_3$-$C_8$ cycloalkyl, $C_1$-$C_{20}$ aminoalkyl, $C_1$-$C_6$ hydroxyalkyl, $C_1$-$C_{12}$ heteroaryl, and $C_1$-$C_{12}$ heterocycle and fluoralkyl;

wherein Z is selected from the group consisting of $Rf_n=(CF_2)_{n-1}CF_3$; n=1-25, —$NO_2$, —CN, —OH, —$CF_3$, —COR, —SH, —OMe, —SMe, —SPh, —COOH, —COOR, —$NH_2$, —NHR, —$NR_2$, $C_2$-$C_{20}$ alkenyl, $C_1$-$C_{20}$ alkoxy, $C_1$-$C_{20}$ alkyl, $C_2$-$C_{20}$ alkynyl, $C_6$-$C_{12}$ aryl, $C_3$-$C_8$ cycloalkyl, $C_1$-$C_{20}$ aminoalkyl, $C_1$-$C_6$ hydroxyalkyl, $C_1$-$C_{12}$ heteroaryl and $C_1$-$C_{12}$ heterocycle;

wherein A is selected from the group consisting of $F^-$, $Cl^-$, $Br^-$, $I^-$, $ClO_4^-$, $PF_6^-$, $N_3^-$, $BF_4^-$, $SbF_6^-$, $BH_4^-$, $(FSO_2)_2N^-$, $(CF_3SO_2)_2N^-$, $(C_2F_5SO_2)_2N^-$, $(CF_3SO_2)_3C^-$, $CF_3SO_3^-$, $ROSO_3^-$, $CF_3COO^-$, $AsF_6^-$, $RCOO^-$, $(CN)_2N^-$, and $NO_3^-$ and $MePhO_2SO^-$; and wherein R is $C_2$-$C_{20}$ alkyl.

2. The phosphonium ionic liquid (11) according to claim 1 wherein $Z=Rf_n$ and Y is not $Rf_n$ and is not fluoroalkyl.

3. The phosphonium ionic liquid (11) according to claim 1 wherein $Y=C_2$-$C_{20}$ alkyl chain, and including a crosslinkable group bonded to a terminal carbon of the $C_2$-$C_{20}$ alkyl chain selected from the group consisting of acrylate, methacrylate, norbornadienyl, styrenyl, alkenyl, alkynyl, maleimidyl and anthracenyl.

4. The phosphonium ionic liquid (11) according to claim 1 wherein $Y=C_2$-$C_{20}$ alkyl chain, and including a polymerizable group bonded to a terminal carbon of the $C_2$-$C_{20}$ alkyl chain selected from the group consisting of acrylate, methacrylate, norbornadienyl, styrenyl, alkenyl, alkynyl, maleimidyl, [1]metalloarenophanyl and [2]metalloarenophanyl.

5. The phosphonium ionic liquid (11) according to claim 1 wherein $Y=C_2$-$C_{20}$ alkyl chain, and including a group bonded to a terminal carbon of the $C_2$-$C_{20}$ alkyl chain selected from the group consisting of —$NO_2$, —CN, —OH, —$CF_3$, —COR, —SH, —OMe, —SMe, —SPh, —SSR, —COOH, —COOR, —$NH_2$, —NHR, —$NR_2$, —Si$(OC_2H_6)_3$, $C_2$-$C_{20}$ alkenyl, $C_1$-$C_{20}$ alkoxy, $C_1$-$C_{20}$ alkyl, $C_2$-$C_{20}$ alkynyl, $C_6$-$C_{20}$ alkyl, $C_6$-$C_{12}$ aryl, $C_3$-$C_8$ cycloalkyl, $C_1$-$C_{20}$ aminoalkyl, $C_1$-$C_6$ hydroxyalkyl, $C_1$-$C_{12}$ heteroaryl and $C_1$-$C_{12}$ heterocycle, fluoralkyl.

6. A fluorous biphasic system comprising the phosphonium ionic liquid (11) according to claim 1 mixed with an organic solvent.

7. The fluorous biphasic system according to claim 6 wherein said organic solvent is selected from the group consisting of, THF, $CH_2Cl_2$, toluene, benzene, $CHCl_3$, hexane, pentane and acetonitrile.

8. A method of forming a coating on a substrate, the method comprising applying the phosphonium ionic liquid (11) as defined by claim 1 to a surface of a substrate to form a hydrophobic or a superhydrophobic coating on the surface.

9. The method of claim 8 wherein the coating is hydrophobic and has a water contact angle between 90° to 150°.

10. The method of claim 8 wherein the coating is superhydrophobic and has a water contact angle of >150°.

11. The method of claim 8, wherein said substrate is selected from the group consisting of metals, polymers, semiconductors, crystalline surfaces, ceramics and glasses.

12. The method of claim 11 wherein said metals are selected from the group consisting of copper, silver, gold, aluminum, indium, chromium, steel, iron, cobalt, stainless steel, titanium, vanadium, and alloys thereof.

13. The method of claim 11 wherein said polymers are selected from the group consisting of polyethylene, polyacrylate, polystyrene.

14. The phosphonium ionic liquid (11) according to claim 3 polymerized to form a solid polymer.

15. The polymerized phosphonium ionic liquid (11) according to claim 14 cast into films, coatings or three dimensional structures.

16. The method of claim 8, wherein the coating formed is an antistatic coating.

17. The method of claim 8, wherein the coating formed is a water vapour barrier, bulk water barrier, aqueous solutions barrier, or a biological liquid barrier.

18. The method of claim 17 wherein said surface is one of an organic light emitting diode and a solar cell.

19. The method of claim 11 wherein said substrate is a nanoparticle.

20. The method of claim 8, wherein said coating is patterned on said substrate in which portions of the surface is coated and portions are not coated.

21. The phosphonium ionic liquid (11) according to claim 1, wherein Y is $C_2$-$C_{20}$ alkyl in which the terminal carbon of the $C_2$-$C_{20}$ alkyl is substituted with acrylate; Z is $Rf_n=(CF_2)_{n-1}CF_3$; n=1-25; and A is selected from the group consisting of $F^-$, $Cl^-$, $Br^-$, $I^-$, $ClO_4^-$, $PF_6^-$, $N_3^-$, $BF_4^-$, $SbF_6^-$, $SH_4^-$, $(FSO_2)_2N^-$, $(CF_3SO_2)_2N^-$, $(C_2F_5SO_2)_2N^-$, $(CF_3SO_2)_3C^-$, $CF_3SO_3^-$, $ROSO_3^-$, $CF_3COO^-$, $AsF_6^-$, $RCOO^-$, $(CN)_2N^-$, and $NO_3^-$ and $MePhO_2SO^-$.

22. The phosphonium ionic liquid (11) according to claim 21, wherein Y is —$CH_2CH_2OC(O)CH$=$CH_2$, Z=$Rf_n$, and n=4 for all n.

* * * * *